(12) United States Patent
Saeki

(10) Patent No.: US 10,094,721 B2
(45) Date of Patent: Oct. 9, 2018

(54) STRESS VISUALIZATION DEVICE AND MECHANICAL PROPERTY VALUE VISUALIZATION DEVICE

(71) Applicant: Osaka City University, Osaka (JP)

(72) Inventor: Souichi Saeki, Osaka (JP)

(73) Assignee: OSAKA CITY UNIVERSITY, Osaka (JP)

( * ) Notice: Subject to any disclaimer, the term of this patent is extended or adjusted under 35 U.S.C. 154(b) by 0 days.

(21) Appl. No.: 15/437,985

(22) Filed: Feb. 21, 2017

(65) Prior Publication Data

US 2017/0160148 A1 Jun. 8, 2017

Related U.S. Application Data

(63) Continuation of application No. PCT/JP2015/073457, filed on Aug. 21, 2015.

(30) Foreign Application Priority Data

Aug. 21, 2014 (JP) ................. 2014-168802

(51) Int. Cl.
*G01L 1/24* (2006.01)
*G01B 9/02* (2006.01)
*G01N 21/21* (2006.01)

(52) U.S. Cl.
CPC ............ *G01L 1/24* (2013.01); *G01B 9/02091* (2013.01); *G01N 21/21* (2013.01)

(58) Field of Classification Search
CPC ...................................................... G01L 1/24
(Continued)

(56) References Cited

U.S. PATENT DOCUMENTS 5,321,501 A * 6/1994 Swanson ............ A61B 1/00096
250/227.27
5,459,570 A * 10/1995 Swanson ............ G01N 21/4795
356/479

(Continued)

FOREIGN PATENT DOCUMENTS

JP 2001228034 A 8/2001
JP 2007244533 A 9/2007
(Continued)

*Primary Examiner* — Tarifur Chowdhury
*Assistant Examiner* — Omar Nixon
(74) *Attorney, Agent, or Firm* — Muncy, Geissler, Olds & Lowe, P.C.

(57) ABSTRACT

A control computation unit causes an optical modulator to change a polarization state to shift a phase of polarized light with which an object is irradiated, computes a spatial gradient of tomographic distribution of phase difference of an interference signal on the basis of phase differences of interference signals each obtained by each phase shift of the polarized light, and visually displays tomographic distribution of spatial gradient in association with tomographic distribution of stress on the display device. The control computation unit computes deformation rate vector distribution at cross-sectional positions of the object on the basis of optical interference signals, and further computes tomographic distribution of strain rate tensor. The control computation unit then computes tomographic distribution of mechanical property value from the tomographic distribution of stress and the tomographic distribution of strain rate tensor, and visually displays the tomographic distribution of mechanical property value.

7 Claims, 17 Drawing Sheets

(58) Field of Classification Search
USPC .......................................................... 356/330
See application file for complete search history.

(56) References Cited

U.S. PATENT DOCUMENTS

| | | | |
|---|---|---|---|
| 6,208,415 B1* | 3/2001 | De Boer | G01N 21/4795 356/450 |
| 6,721,094 B1* | 4/2004 | Sinclair | G01B 9/04 356/445 |
| 2001/0028451 A1 | 10/2001 | Kanno et al. | |
| 2008/0123079 A1 | 5/2008 | Numata et al. | |
| 2010/0128276 A1* | 5/2010 | De Groot | G01B 11/2441 356/450 |
| 2014/0115022 A1 | 4/2014 | Yasuno et al. | |

FOREIGN PATENT DOCUMENTS

| | | |
|---|---|---|
| JP | 20080134186 A | 6/2008 |
| JP | 2013019773 A | 1/2013 |
| JP | 2015075383 A | 4/2015 |

\* cited by examiner $$S_3/S_0(x,z) = A(x,z)\cos(2\Phi(x,z) + \delta EOM(V)) + B(x,z)$$
Fixed  Fixed  Fixed  Fixed

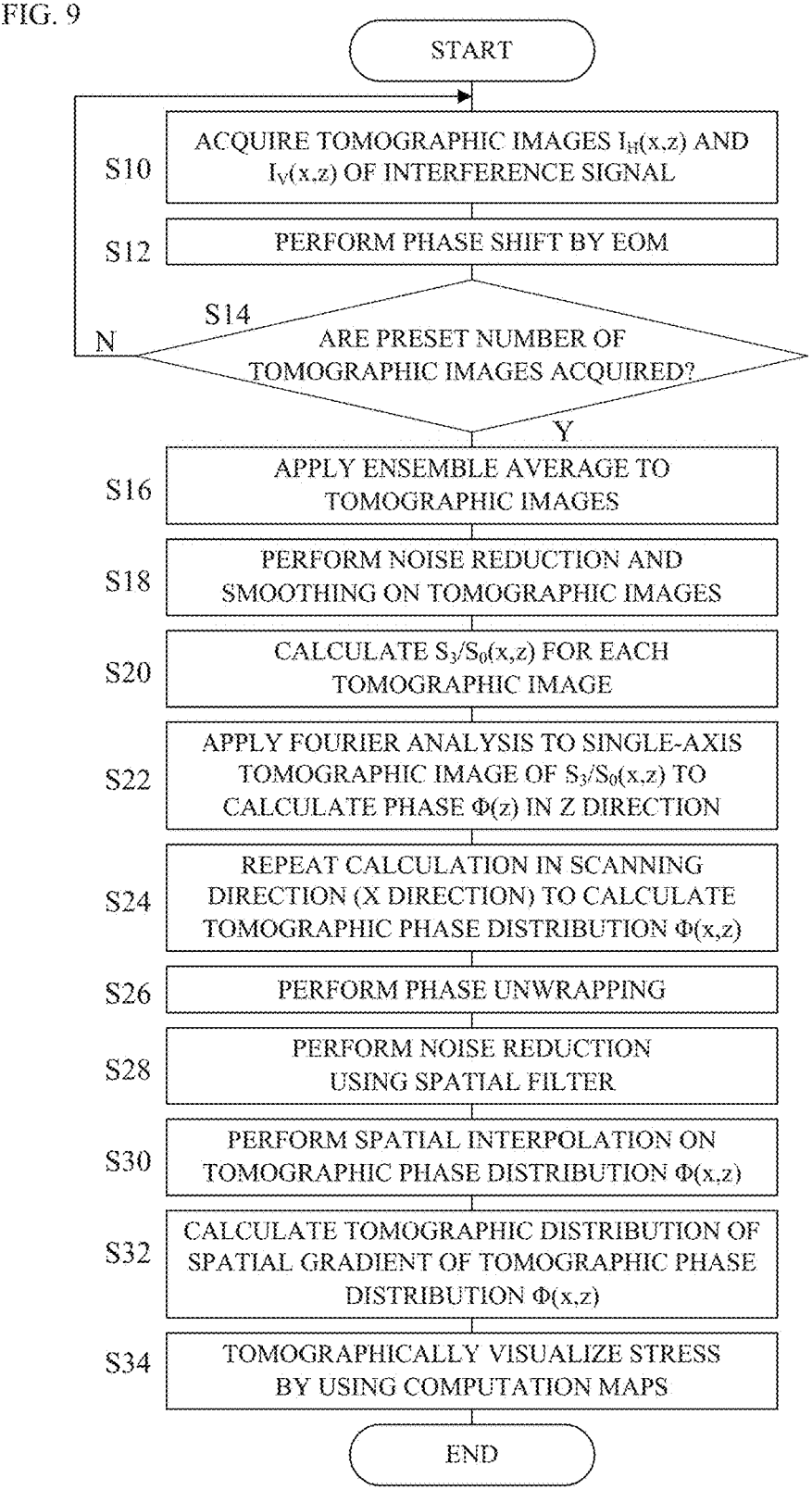

TIME DIRECTION

TIME DIRECTION

STRESS VISUALIZATION DEVICE AND MECHANICAL PROPERTY VALUE VISUALIZATION DEVICE

CROSS-REFERENCE TO RELATED APPLICATIONS

This application is a continuation application of International Application No. PCT/JP2015/073457, filed on Aug. 21, 2015, which claims priority to and the benefit of Japanese Patent Application No. 2014-168802, filed on Aug. 21, 2014. The contents of these applications are incorporated herein by reference in their entirety.

BACKGROUND OF INVENTION

1. Field

The present invention relates to a stress visualization device. More particularly, the invention relates to a device for measuring and visualizing distribution of stress applied to an object or internal stress of an object by an optical method. The invention also relates to a device for visualizing tomographic distribution (cross-sectional distribution) of mechanical property value of an object.

2. Description of Related Art

In recent years, composite materials have rapidly expanded their applications in various fields including aviation and space, automobiles, electronic components, and medical equipment. Such composite materials have diversified in shape and size, and have been miniaturized. Since a composite material has an interface of a base material and a reinforcing material, microscale internal defects such as interfacial peeling and transverse cracks may be intricately interrelated. This leads to fracture of the composite material. There have therefore been demands for development of non-destructive measurement techniques enabling quantitative evaluation of mechanical conditions such as stress concentration inside a material.

A method of measuring residual stress on the surface of an object to be inspected in a non-destructive and non-contact manner by an optical technique is proposed as one of such measurement techniques (refer to JP 2008-134186 A, for example). This technique includes irradiating the surface of an object with laser light for heating and laser light for deformation quantity measurement, obtaining the total deformation between before and after thermal stress relief of an inspection area by optical interferometric measurement, and subtracting a deformation quantity induced by a thermal strain from the total deformation quantity, to calculate a deformation quantity induced by residual stress. The technique further includes dividing the deformation quantity due to the residual stress by the difference in Young's modulus between before and after heating, to calculate the residual stress.

RELATED ART LIST (1) JP 2008-134186 A

With the technology disclosed in JP 2008-134186 A, however, although the stress distribution on the surface of an object can be obtained, the stress distribution inside the object cannot be obtained. Furthermore, a heating device is required in addition to an interferometer for stress measurement, which results in a large-scale measurement system as a whole. Furthermore, since thermal stress is externally applied to the object, this may alter the properties of the object even though the alteration is within an elastic deformation range.

SUMMARY OF INVENTION

In view of the above and other circumstances, one purpose of the present invention is to provide a technology allowing simple measurement and visualization of distribution of stress applied to, or internal stress of, an object by an optical technique.

An embodiment of the present invention provides a stress visualization device for tomographically visualizing stress in an object to be measured. The stress visualization device includes: a light source configured to emit light; a polarizer configured to linearly polarize the light emitted from the light source; a beam splitter configured to split the linearly polarized light into a first beam directed to an object arm including the object and a second beam directed to a reference arm including a reference mirror; an optical modulator provided on the object arm and configured to change a polarization state of the linearly polarized light; an optical detection device configured to detect interference light, resulting from superimposition of object light reflected by the object and reference light reflected by the reference mirror, as an optical interference signal, and separate the interference signal into a horizontal polarization component and a vertical polarization component; a control computation unit configured to adjust the polarization state by controlling the optical modulator, and compute distribution of stress at cross-sectional positions, each defined by a position in a depth direction and a position in a direction orthogonal to the depth direction of the object, on a basis of a phase difference between the horizontal polarization component and the vertical polarization component of the interference signal detected by the optical detection device; and a display device configured to display tomographically visualized stress distribution of the object on a basis of a computation result of the control computation unit.

The control computation unit causes the optical modulator to change the polarization state to shift a phase of polarized light with which the object is irradiated, computes the phase difference for the interference signal obtained by each phase shift of the polarized light, computes spatial gradients of tomographic distribution of phase difference on a basis of the computed phase difference, and visually displays tomographic distribution of spatial gradient in association with tomographic distribution of stress on the display device.

According to this embodiment, so-called polarization sensitive optical coherence tomography (hereinafter referred to as "PS-OCT") is used for measurement of stress distribution of an object. This allows tomographic measurement of distribution of phase difference between two polarized light waves inside the object, calculation of stress distribution from spatial frequency of interference fringes to appear in a tomographic image of the phase difference distribution, and visualization of the stress distribution. Thus, tomographic distribution of stress can be readily measured without the need to separately load stress for stress measurement on the object. In particular, phase shift of polarized light waves allows stress measurement to be carried out at any position inside an object at the spatial resolution of the OCT.

Certain aspects of the present invention provide technologies allowing simpler measurement of distribution of stress applied to, or residual stress of, an object by an optical technique.

BRIEF DESCRIPTION OF DRAWINGS

FIG. 9 is a flowchart schematically illustrating procedures of a stress visualization process performed by a control computation unit;

DETAILED DESCRIPTION

[First Embodiment]

A principle of a stress visualization method according to a first embodiment will now be described.

Figure 1:
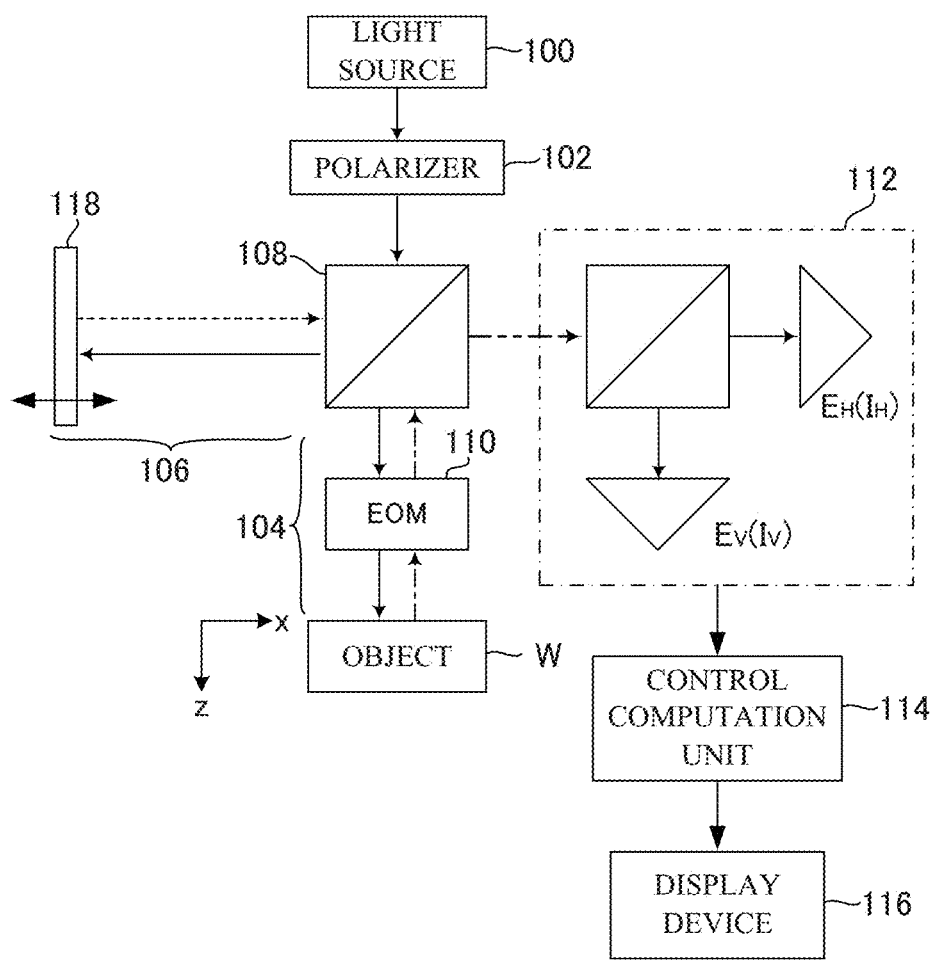
FIG. 1 is a schematic diagram illustrating a configuration of a stress visualization device according to a first embodiment.

FIG. 1 is a schematic diagram illustrating a configuration of a stress visualization device according to the first embodiment. The stress visualization device uses the PS-OCT using two polarized light waves to perform tomographic (cross-sectional) stress measurement on an object W to be measured. The device includes a light source 100, a polarizer 102, an object arm 104, a reference arm 106, a beam splitter 108, an electro-optic modulator (hereinafter referred to as an "EOM") 110, an optical detection device 112, a control computation unit 114, and a display device 116. While an optical system based on a Michelson interferometer is presented in the example illustrated in FIG. 1, other optical systems such as a Mach-Zehnder interferometer may alternatively be used.

A light source capable of emitting low coherence light (low temporal coherence light) is used for the light source 100. Alternatively, a light source capable of emitting wavelength-swept light may be used. While time domain OCT (TD-OCT) according to classification of optical delay scanning is illustrated in the example of FIG. 1, other types of OCT such as spectral domain OCT (SD-OCT) or swept source OCT (SS-OCT) may be used instead.

Note that the "TD-OCT" is a technique of performing optical delay scanning by driving a reference mirror 118 at the reference arm 106. The TD-OCT measures interference light of light from the reference arm 106 and backscattered light from the object arm 104, and obtains reflected light intensity in the depth direction of the object W. The "SD-OCT" is a technique of splitting the interference light by a spectrometer and performing Fourier transform to obtain the reflected light intensity. The SD-OCT does not require mechanical optical delay scanning like the TD-OCT. The "SS-OCT" is a technique of using pseudo-low coherence light (broadband light source). The SS-OCT performs Fourier transform to obtain the reflected light intensity similarly without performing mechanical optical delay scanning.

Examples of the object W include a polymer-based material such as a polymeric resin material. Alternatively, a crystalline material such as plastic may be used. The device is particularly effective in microscale non-destructive inspection. The object W may be any material having a reflecting structure (such as an interface) inside the material. The device is also effective for an opaque material such as a composite material of resin containing scatterers such as nanoparticles.

The polarizer 102 is installed to transform light emitted from the light source 100 into desired linearly polarized light. The linearly polarized light is split by the beam splitter 108, one of the resulting beams is directed to the object arm 104 and the other of the resulting beams is directed to the reference arm 106.

The linearly polarized light beam directed to the object arm 104 passes through the EOM 110, where the polarization state of the light beam is adjusted. The beam is converted to circularly polarized light or elliptically polarized light with which the object W is irradiated. The irradiation light is reflected as backscattered light at a cross section of the object W at a depth corresponding to the optical distance of the reference arm 106. The reflected light returns as object light to the beam splitter 108. In the meantime, the linearly polarized light beam directed to the reference arm 106 is reflected by the reference mirror 118. The reflected light returns as reference light to the beam splitter 108. The object light and the reference light are combined (superimposed) by the beam splitter 108, and interference light of the object light and the reference light is detected by the optical detection device 112. In a case where a Mach-Zehnder interferometer is used, the object light and the reference light are combined without returning to the beam splitter.

The optical detection device 112 separates the interference light into two polarized light waves, which are a horizontal polarization component $E_H$ and a vertical polarization component $E_V$, to detect the horizontal polarization component $I_H(x,z)$ and the vertical polarization component $I_V(x,z)$ of interference light intensity. Herein, spatial coordinates are defined such that the optical axis direction of light with which the object W is irradiated is a z axis, and directions orthogonal to the optical axis are an x axis and a y axis. The z axis represents the depth direction of the object W, the x axis represents the scanning direction of the light with which the object W is irradiated. In the present embodiment, for visualization of a tomographic image along an x-z plane of the object W, the interference light intensity is also detected in a form of x and z components.

The control computation unit 114 computes stress distribution at cross-sectional positions specified on the x-z plane of the object W on the basis of detected values from the optical detection device 112. In order to increase the resolution of a tomographic image measured by the computation, a phase shifting technique is used. This technique appropriately shifts the polarization state (a phase difference between a fast axis and a slow axis) of light with which the object W is irradiated. The phase shifting is performed by control of the EOM 110.

The display device 116 is constituted by a liquid crystal display, for example, and displays, on a screen, stress distribution computed by the control computation unit 114 in a form of a tomographic image of the object W.

Figure 2:
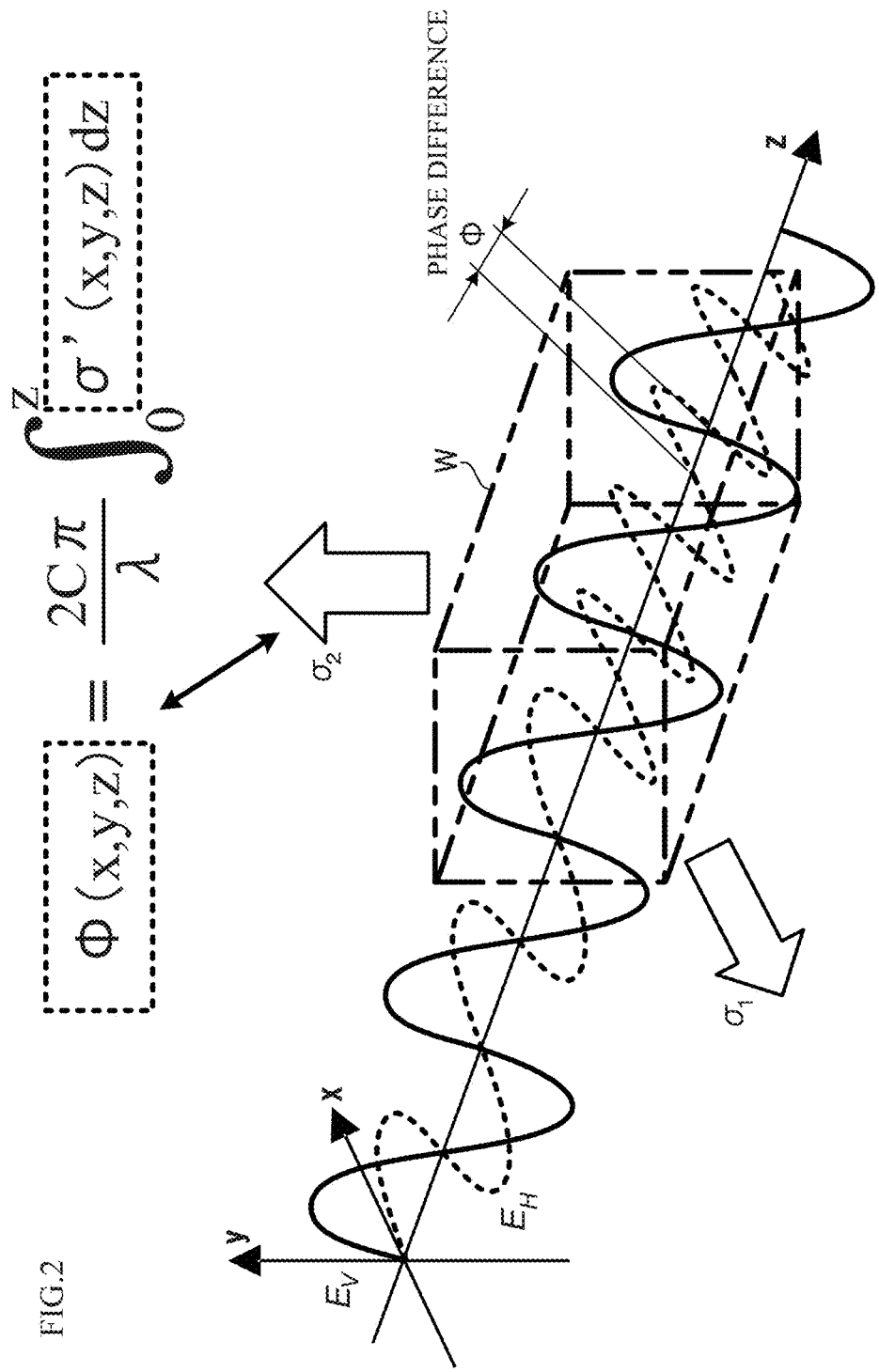
FIG. 2 is an explanatory diagram illustrating a principle of tomographic stress measurement using the PS-OCT.
Figure 3:
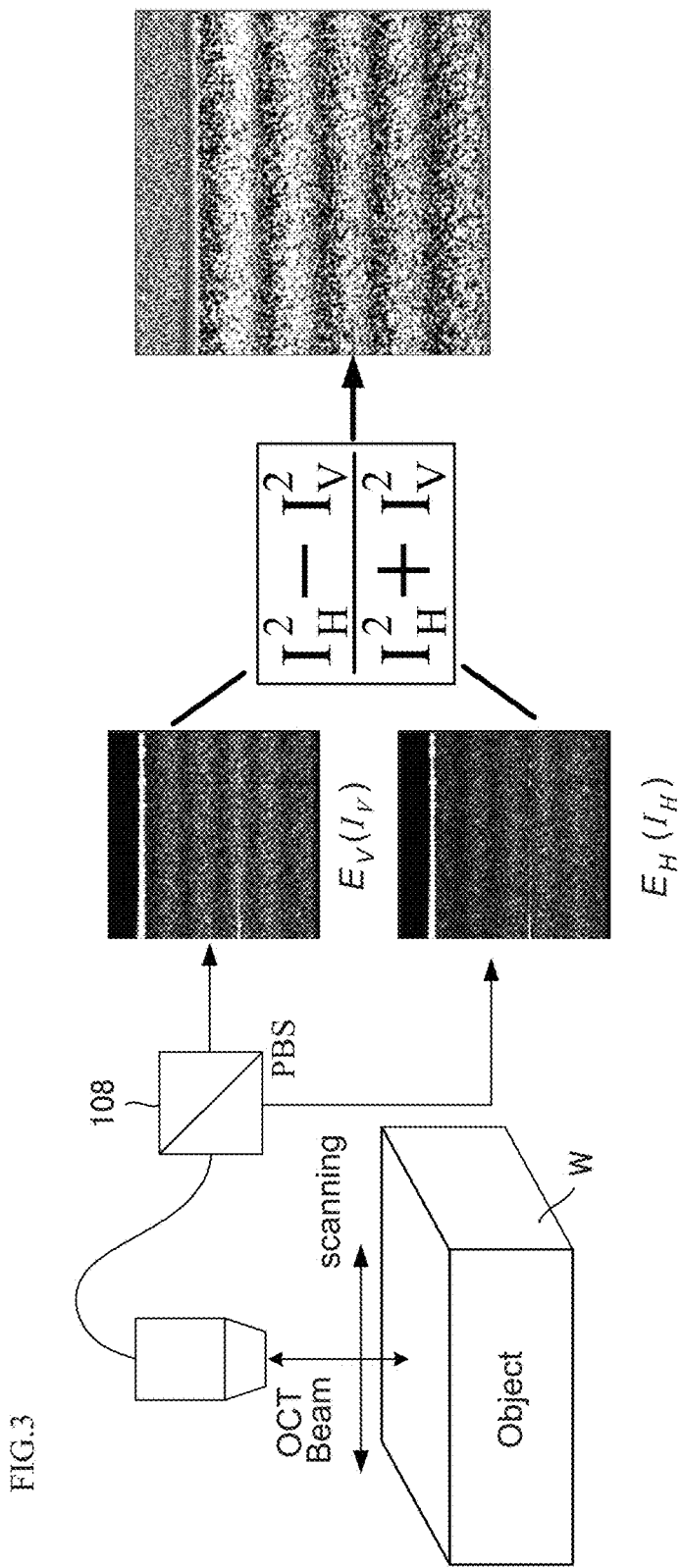
FIG. 3 is an explanatory diagram illustrating the principle of the tomographic stress measurement using the PS-OCT.
Figure 4:
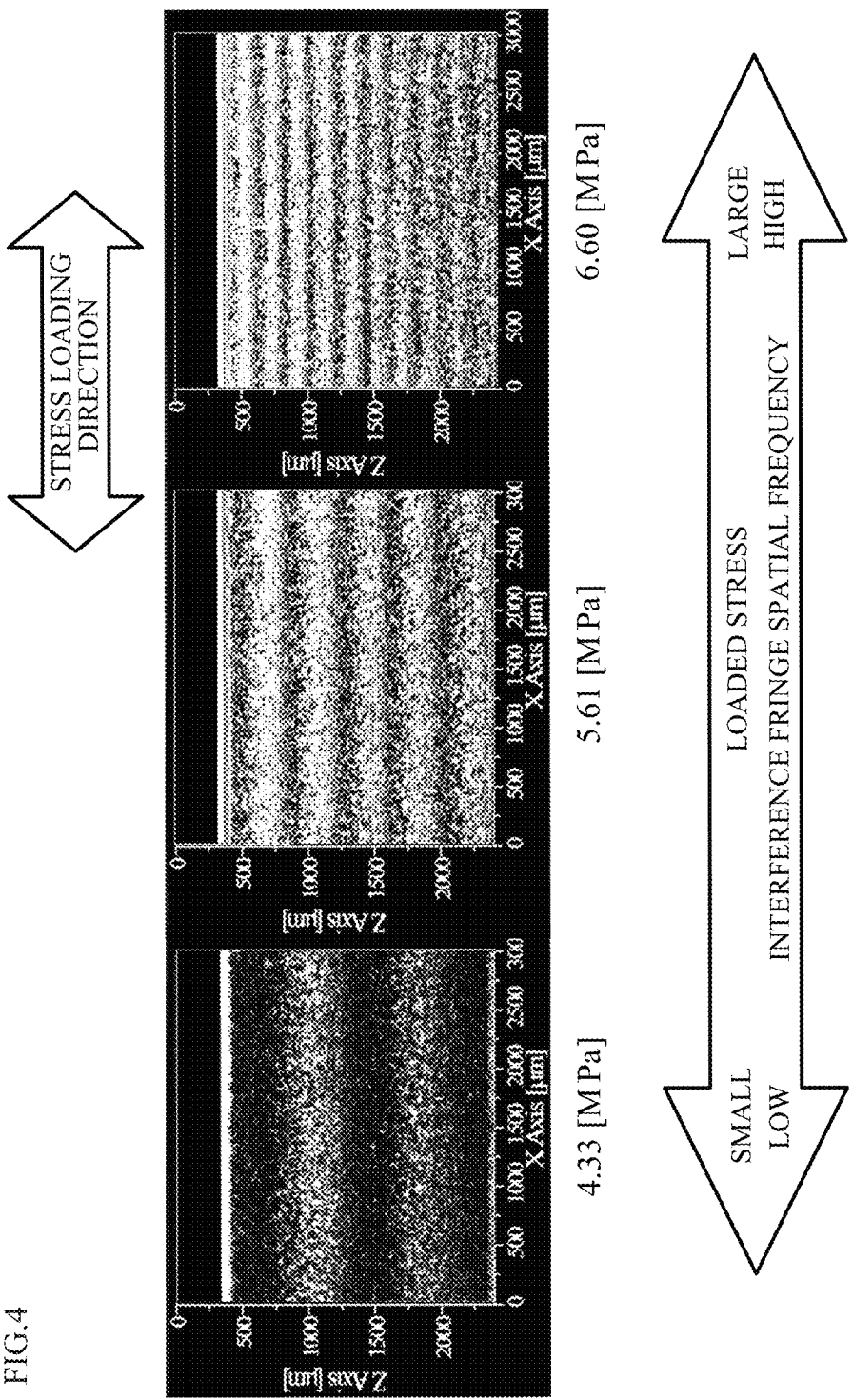
FIG. 4 is an explanatory diagram illustrating the principle of the tomographic stress measurement using the PS-OCT.

A principle of the computation will now be explained in sequence. FIGS. 2 to 4 are explanatory diagrams illustrating the principle of tomographic stress measurement using the PS-OCT. The tomographic measurement of the present embodiment is conducted by applying the PS-OCT to a photoelastic technique of scattered light for measuring stress distribution three-dimensionally. The photoelastic technique uses backscattered light resulting from irradiating the object W with polarized light waves to measure a phase difference between light waves inside an object W.

As illustrated in FIG. 2, according to the photoelastic technique, spatial coordinates (x,y,z) are set for an object W in a three-dimensional stress field. The incident axis of polarized light waves is set as a z axis. An x axis and a y axis are set to be orthogonal to the z axis. The object W is a birefringent polymer material. Thus, when circularly polarized light is incident on the object W, the polarization state of its polarized waves changes. The change in the polarization state is considered to be mainly due to a change in refractive index at an x-y cross section.

Thus, when principal stress acting on the object W has changed or when a local change in principal stress is present inside the object W, the change appears as a phase difference $\Phi(x,y,z)$ between the horizontal polarization component $E_H$ and the vertical polarization component $E_V$ of interference light. In other words, interference signals corresponding to the two polarized light waves are obtained according to the phase difference $\Phi(x,y,z)$ between the two polarized light waves. The phase difference $\Phi(x,y,z)$ is expressed by the following expression (1).

$$\Phi(x, y, z) = \frac{2C\pi}{\lambda} \int_0^z \sigma'(x, y, z)dz \qquad (1)$$

In the expression (1), $\lambda$ represents the wavelength of light incident on the object W, $\sigma'(x,y,z)$ represents a difference (principal stress difference) between principal stresses $\sigma 1$ and $\sigma 2$ acting at the x-y cross section of the object W. C represents a photoelastic constant. Specifically, the phase difference $\Phi(x,y,z)$ between light waves traveling inside the object W is proportional to integration of the principal stress difference $\sigma'(x,y,z)$ along the optical path back and forth to the cross section where an interference signal is obtained on the basis of a mechanical birefringence effect.

According to the PS-OCT of the present embodiment, the horizontal polarization component $I_H(x,z)$ and the vertical polarization component $I_V(x,z)$ of the interference light intensity satisfy the following expressions (2) and (3).

$$I_H(x, z) = \sqrt{R(x, z)} \sin\{\Phi(x, z)\}\exp\left(-\frac{\Delta l_0}{l_c}\right)^2 \qquad (2)$$

$$I_V(x, z) = \sqrt{R(x, z)} \cos\{\Phi(x, z)\}\exp\left(-\frac{\Delta l_0}{l_c}\right)^2 \qquad (3)$$

In the expressions (2) and (3), R(x,z) represents reflectance distribution, $\Phi(x,z)$ represents x and z components of the phase difference $\Phi(x,y,z)$, $l_c$ represents the coherence length of emitted light. $\Delta l_0$ represents the difference in optical path length between the object arm 104 and the reference arm 106.

In this case, $S_0$ and $S_3$ among components of Stokes parameters defining polarization states can be calculated on the basis of the expressions (4) and (5) below. Note that $S_0$ represents the total intensity of measured light, and $S_3$ represents the intensity difference between linearly polarized orthogonal components, which are well known and detailed description thereof is therefore omitted here.

$$S_0(x,z)=I_H^2(x,z)+I_V^2(x,z)\propto R(x,z) \qquad (4)$$

$$S_3(x,z)=I_H^2(x,z)-I_V^2(x,z)=R(x,z)\cos\{2\Phi(x,z)\} \qquad (5)$$

Here, $S_0(x,z)$ is divided by $S_0(x,z)$, so that information on reflection intensity is removed and a cosine function dependent only on the phase difference $\Phi(x,z)$ between polarized waves dependent on the mechanical birefringence effect is extracted as expressed by the expression (6).

$$S_3/S_0(x, z) = \frac{I_H^2(x, z) - I_V^2(x, z)}{I_H^2(x, z) + I_V^2(x, z)} = \cos(2\Phi(x, z)) \qquad (6)$$

Thus, the expression (1) shows that the phase difference distribution $\Phi(x,z)$ is proportional to an integrated value of principal stress difference distribution $\sigma'(x,z)$ at the x-y cross section perpendicular to the optical axis. In addition, the expression (6) shows that the intensity distribution of a Stokes parameter map $S_3/S_0(x,z)$ appears as a fringe pattern of the cosine function of the phase difference distribution $\Phi(x,z)$. Thus, as illustrated in FIG. 3, detection of the spatial frequency distribution (calculation of the spatial gradient) of interference fringes in $S_3/S_0(x,z)$ allows tomographic visualization of the principal stress difference distribution $\sigma'(x,z)$. Note that the phase difference distribution $\Phi(x,z)$ can also be regarded as a phase of a cosine function expressing the Stokes parameter map $S_3/S_0(x,z)$.

FIG. 4 shows examples of tomographic images obtained when tensile stress in the x direction is applied to the object W. As illustrated in FIG. 4, as the stress applied to the object W is greater, the spatial frequency of interference fringes is higher. The tomographic images thus visualize the stress distribution of the object W. In FIG. 4, cases where an external load is applied to the object W are shown. In a case where no external load is applied to an object W but internal residual stress acts inside the object W, the residual stress can also be tomographically measured and visualized.

In the present embodiment, since beam scanning is performed one-dimensionally in the x direction, two-dimensional stress distribution based on two-dimensional tomographic measurement is visualized. Alternatively, if a beam is scanned two-dimensionally over the x-y plane, three-dimensional tomographic measurement can be performed and three-dimensional stress distribution can be visualized.

For obtaining detailed stress distribution with the techniques described above, the spatial frequency of the interference fringes in the Stokes parameter map $S_3/S_0(x,z)$ needs to be calculated at high spatial resolution. Thus, in the present embodiment, the phase shifting technique described below is incorporated. The phase shifting technique is a technique of analyzing the spatial frequency of interference fringes by using different images of interference fringes with shifted phases and performing nonlinear parameter identification while referring to the phase shift.

In the phase shifting process, tomographic images of the interference fringes in the Stokes parameter map $S_3/S_0(x,z)$ with shifted phases are taken. In this process, the EOM 110 is used to cause light, which is obtained by shifting circularly polarized light by a phase difference $\delta_{EOM}(V)$, to be incident. In this case, the obtained Stokes parameter map $S_3/S_0(x,z)$ becomes as expressed by the following expression (7) obtained by converting the expression (6).

$$S_3/S_0(x,z) = \tag{7}$$

$$\frac{I_H^2(x,z) - I_V^2(x,z)}{I_H^2(x,z) + I_V^2(x,z)} = A(x,z)\cos(2\Phi(x,z) + \delta_{EOM}(V)) + B(x,z)$$

$$A(x,z) = \sum_{i=0}^{k-1} S_3/S_0(x,z,\delta_i)\sin\left(2\pi\frac{i}{k}\right)$$

$$B(x,z) = \sum_{i=0}^{k-1} S_3/S_0(x,z,\delta_i)\cos\left(2\pi\frac{i}{k}\right)$$

$$2\Phi(x,z) = \tan^{-1}\left(\frac{A(x,z)}{B(x,z)}\right)$$

In the expression (7), a proportional coefficient $A(x,z)$ and a constant $B(x,z)$ are defined. These are used, when the phase shifting technique is applied, to obtain the phase difference distribution $\Phi(x,z)$, obtain the spatial gradient of the phase difference distribution $\Phi(x,z)$, and more accurately obtain the principal stress difference $\sigma'(x,z)$ from the spatial gradient. $A(x,z)$ and $B(x,z)$ can be obtained by the least-squares method, for example. Note that the phase difference distribution $\Phi(x,z)$ is calculated as tomographic phase distribution $\Phi(x,z)$ in the Stokes parameter map $S_3/S_0(x,z)$.

Figure 5A:
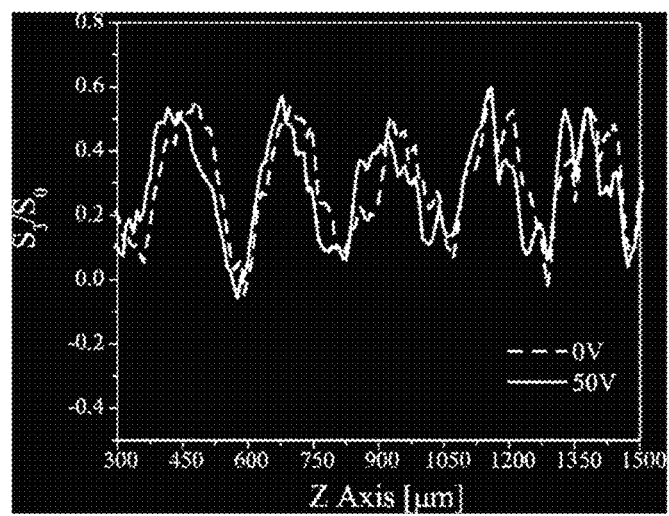
FIGS. 5A to 5C are graphs showing results of computing changes of $S_3/S_0$ in cases where phase shifting is performed with different voltages applied to an optical modulator.
Figure 5B:
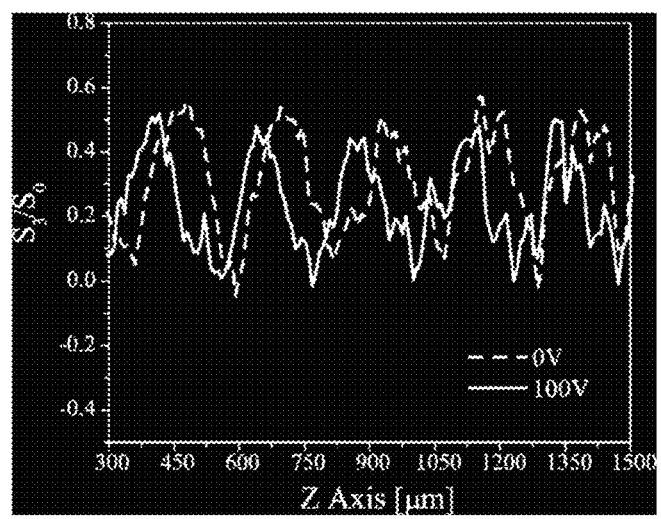
Figure 5C:
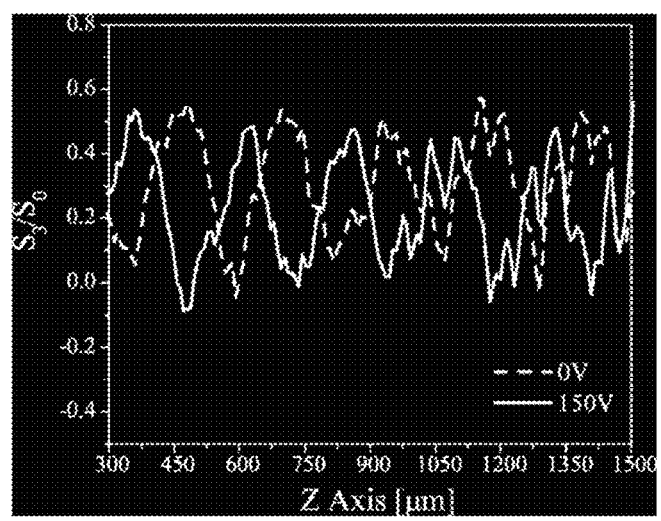

FIGS. 5A to 5C are graphs showing results of computing changes of $S_3/S_0$ in cases where phase shifting is performed with different voltages applied to the EOM 110. FIG. 5A shows a case where the applied voltage is 50 V, FIG. 5B shows a case where the applied voltage is 100 V, and FIG. 5C shows a case where the applied voltage is 150 V. In the graphs, the horizontal axis represents the depth in the z axis direction of the object W, and the vertical axis represents the value of $S_3/S_0(x,z)$. In FIGS. 5A to 5C, solid lines represent applied voltages. In FIGS. 5A to 5C, wavy lines represent computation results with a reference voltage of 0 V, that is, when the EOM 110 is not used. The computation averages the Stokes parameter map $S_3/S_0(x,z)$ in the x-axis direction, and calculates variation in phase difference in the z-axis direction.

In this case, a tensile stress of 4.5 MPa is externally loaded in the x-axis direction on the object W. In addition, the polarization state is set so that the polarization state of light incident on the object W is circular polarization when the applied voltage is 0 V. The results in FIGS. 5A to 5C show that a change in the voltage applied to the EOM 110 allows the phases of polarized waves to be shifted at respective measurement positions (x,z) while the outline of the Stokes parameter map $S_3/S_0(x,z)$ is maintained.

Figure 6:
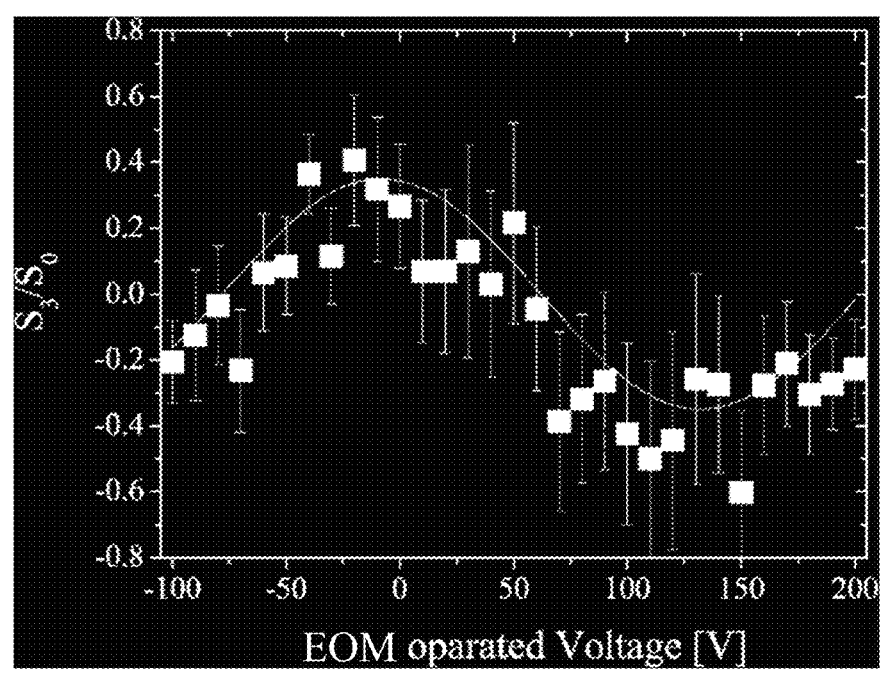
FIG. 6 is a graph showing variation in $S_3/S_0$ at a specific measurement position (x,z) when phase shifting is performed with different voltages applied to the optical modulator.

FIG. 6 is a graph showing variation in $S_3/S_0$ at a specific measurement position (x,z) when phase shifting is performed with different voltages applied to the EOM 110. In FIG. 6, the horizontal axis represents the voltage applied to the EOM 110, and the vertical axis represents the value of $S_3/S_0(x,z)$. The computation result is obtained with the coordinates (x,z) fixed to specific coordinates in the expression (7).

The computation result shows that the Stokes parameter map $S_3/S_0(x,z)$ at the specific coordinates with respect to the voltage applied to the EOM 110 changes according to a sine function. Thus, the phase shifting technique is applicable to results of measurement by the PS-OCT, and phase shift of polarized light waves allows calculation of stress at any cross-sectional position. This enables stress measurement at any position inside an object W at the spatial resolution of the OCT, and achieves a very high resolution in visualization of stress distribution.

Figure 7A:
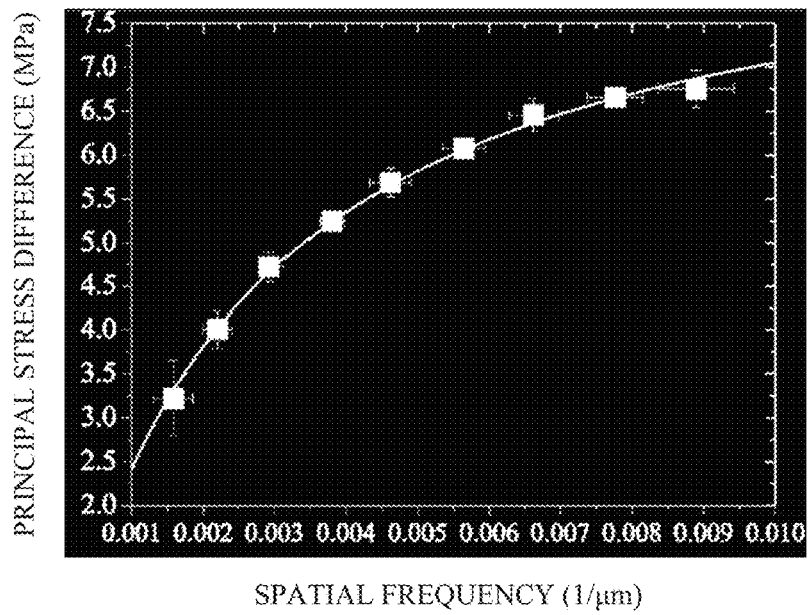
FIGS. 7A and 7B are graphs showing computation maps used in stress measurement with the PS-OCT.
Figure 7B:
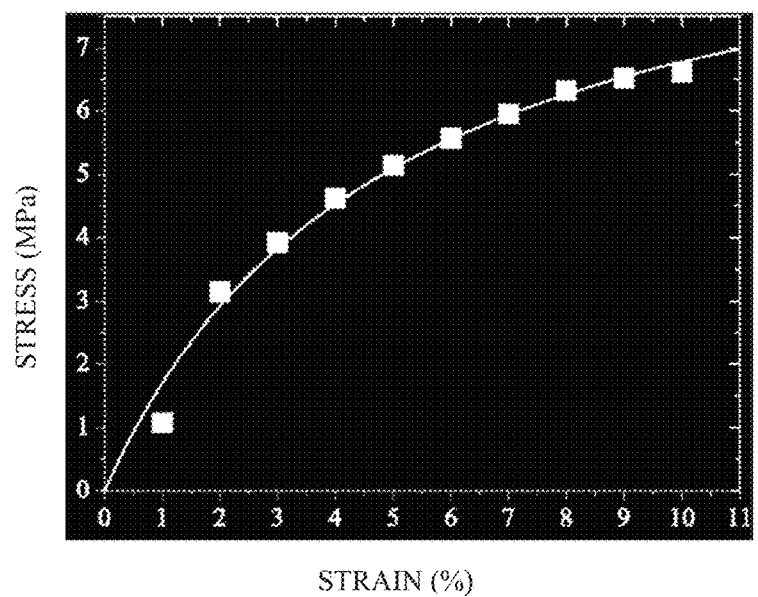

FIGS. 7A and 7B are graphs showing computation maps used in stress measurement by the PS-OCT. FIG. 7A shows a computation map applied to a material. In FIG. 7A, the horizontal axis represents spatial frequency (1/µm) obtained from measurement of $S_3/S_0(x,z)$, and the vertical axis represents a principal stress difference $\sigma'(x,z)$ (MPa) at the position of the measurement. FIG. 7B shows a known stress-strain diagram of the material. In FIG. 7B, the horizontal axis represents strain (%), and the vertical axis represents stress (MPa).

As illustrated in FIG. 7A, in the present embodiment, the computation map associates the spatial frequency obtained from measurement of $S_3/S_0(x,z)$ and the principal stress difference $\sigma'(x,z)$ at the position of the measurement. The spatial frequency represents the spatial gradient of tomographic phase distribution $\Phi(x,z)$, which will be described below. The computation map is provided for each material that can be the object W. The computation map is obtained by experimentally obtaining a calibration curve showing a correlation between stress loaded on the object W and the spatial frequency of interference fringes obtained by the PS-OCT. Comparison between FIGS. 7A and 7B shows that the curves in FIGS. 7A and 7B match each other with high precision.

An example according to the present embodiment will now be described in detail with reference to the drawings.

Figure 8:
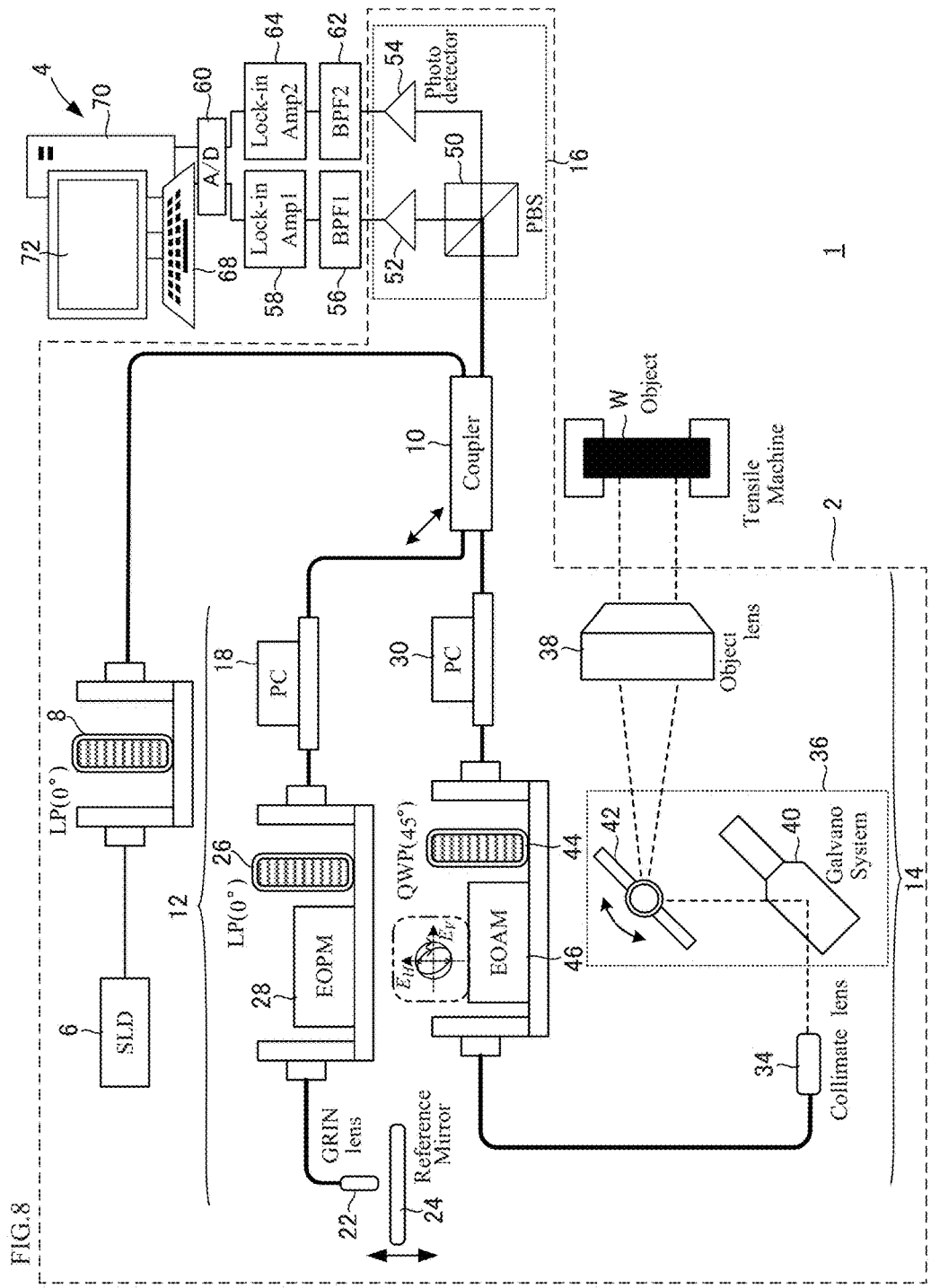
FIG. 8 is a diagram illustrating an entire configuration of a stress visualization device according to an example.

FIG. 8 is a diagram illustrating the entire configuration of a stress visualization device according to the example. The stress visualization device 1 is a system configured to compute stress distribution of an object W to be measured by using TD-PS-OCT based on the Michelson interference optical system. The stress visualization device 1 includes an optical system 2 configured to perform optical processing by the OCT, and a control computation unit 4 configured to compute the stress distribution of an object W on the basis of the processing result. The optical system 2 includes optical components such as a light source 6, a polarizer 8, a coupler 10, a reference arm 12, an object arm 14, and an optical detection device 16. The optical components are connected with one another by fibers.

The light source 6 is a broadband light source constituted by a super luminescent diode (hereinafter referred to as an "SLD"). The SLD emits high-intensity, low-coherence, near-infrared light. In a modification, other light sources capable of emitting low coherence light may be used.

The polarizer 8 is a linear polarizer (hereinafter referred to as an "LP") that converts light from the light source 6 into linearly polarized light. The polarizer 8 is disposed between the light source 6 and the coupler 10. The coupler 10 has a function as a beam splitter that splits light from the light source 6 toward the reference arm 12 and toward the object arm 14, and a function of combining light returning from the reference arm 12 and light returning from the object arm 14 and causing the lights interfere with each other.

The reference arm 12 includes a polarization controller (hereinafter referred to as a "PC") 18, an LP 26, an EOM 28, and a focusing lens 22, which are connected in this order. The focusing lens 22 is opposed to a reference mirror 24. The LP 26 adjusts the polarization state of light guided to the reference arm 12 via the coupler 10. The EOM 28 is configured to linearly change the applied voltage so that a single, high carrier frequency can be obtained. The EOM 28 is also called an electro-optic phase modulator (hereinafter also referred to as an "EOPM 28"). This enables highly sensitive heterodyne detection of an interference signal obtained by the OCT.

The LP 26 cooperates with the PC 18 so that the intensity of light returning from the reference arm 12 does not change even though the polarization state of the light is modulated by the EOPM 28. Specifically, the PC 18 adjusts the polarization state of reference light returning from the reference mirror 24 to linear polarization of 45 degrees when the returning reference light is incident on the coupler 10.

The object arm 14 includes a PC 30, a quarter wave plate (hereinafter referred to as "QWP" 44, an EOM 46, a collimating lens 34, a Galvano system 36, and an object lens 38, which are connected in this order. The Galvano system 36 includes a fixed mirror 40 and a galvanometer mirror 42. The object lens 38 is opposed to the object W. Light incident on the object arm 14 via the coupler 10 is scanned in the x-axis direction by the two-axis galvanometer mirror 42, and directed to the object W. Light reflected by the object W returns as object light to the coupler 10, is superimposed on reference light, and transmitted as interference light to the optical detection device 16.

The PC 30 adjusts the polarization state of light guided from the coupler 10 to the object arm 14 to circular polarization or elliptical polarization. The QWP converts 45-degree linearly polarized light passing through the QWP 44 into circularly polarized light by shifting the phase difference between the fast axis and the slow axis by a quarter wave. The EOM 46 is configured to change the polarization state of transmitted light to any state according to the applied voltage. The EOM 46 is also called an electro-optic amplitude modulator (EOAM). Thus, circularly polarized light passing through the QWP 44 can be converted to elliptically polarized light, and the phase difference between the fast axis and the slow axis of the elliptically polarized light can be changed according to the applied voltage.

The optical detection device 16 includes a polarization beam splitter (hereinafter referred to as a "PBS") 50, a photodetector 52 (functioning as a "first photodetector"), and a photodetector 54 (functioning as a "second photodetector"). The PBS 50 splits interference light resulting from combination by the coupler 10 into a horizontal polarization component $E_H$ and a vertical polarization component $E_V$, and outputs the horizontal polarization component $E_H$ and the vertical polarization component $E_V$ to the photodetectors 52 and 54, respectively. The photodetector 52 then detects a horizontal polarization component $I_H(x,z)$ of the interference light intensity, and the photodetector 54 detects a vertical polarization component $I_V(x,z)$ of the interference light intensity. The detections are performed simultaneously. The horizontal polarization component $I_H(x,z)$ is input to the control computation unit 4 via a band-pass filter (hereinafter referred to as a "BPF") 56, an amplifier 58 (lock-in amp) and an AD converter 60. The vertical polarization component $I_V(x,z)$ is input to the control computation unit 4 via a BPF 62, an amplifier 64 (lock-in amp), and the AD converter 60.

The control computation unit 4 is constituted by a personal computer in the present example, and includes an input device 68 for receiving various user inputs, a computation unit 70 configured to perform computation according to computation programs for image processing, and a display device 72 to display computation results. The computation unit 70 includes a CPU, a ROM, a RAM, a hard disk, and the like, and uses the hardware and software to perform control of the entire optical system 2 and computation for image output based on results of optical processing.

The control computation unit 4 performs phase shift calculation on results of measurement by the PS-OCT on the basis of the above-described principle to calculate the spatial frequency of the Stokes parameter map $S_3/S_0(x,z)$. The control computation unit 4 then refers to the computation map shown in FIG. 7 by using the calculated spatial frequency to calculate stress acting on a given position of the object W, and displays the calculated stress on the display device 72.

FIG. 9 is a flowchart schematically illustrating procedures of a stress visualization process performed by the control computation unit 4. In the stress visualization process, the control computation unit 4 first sets the voltage applied to the EOM 46 to a preset initial value (for example, 0 V in an electrically off state), and then acquires tomographic images by the PS-OCT. In other words, the control computation unit 4 acquires a horizontal polarization component $I_H(x,z)$ and a vertical polarization component $I_V(x,z)$ of an interference signal (interference light intensity) (S10). Subsequently, the control computation unit 4 changes the voltage applied to the EOM 46 to shift the phases of polarized waves, and acquires tomographic images (S12). The phase shift and the acquisition of tomographic images are repeated a preset number of times (No in S14).

When the preset number of tomographic images are acquired (Y in S14), the control computation unit 4 then applies an ensemble average as preprocessing to the tomographic images (S16), and performs noise reduction and smoothing using the moving least-squares method (S18). The control computation unit 4 then calculates a Stokes parameter map $S_3/S_0(x,z)$ for each of the tomographic images (S20).

The control computation unit 4 then performs the following processing on the Stokes parameter map $S_3/S_0(x,z)$ of each of the tomographic images. The control computation unit 4 applies Fourier analysis or the least squares method to a single-axis tomographic image (one tomographic image along an x coordinate scanned by the OCT) of $S_3/S_0(x,z)$ to calculate its phase $\Phi(z)$ in the z direction (depth direction) (S22). This processing is performed on each of x coordinates in the x direction (the scanning direction of the OCT) to calculate tomographic phase distribution $\Phi(x,z)$ (S24). As a result of this processing the coefficients of $S_3/S_0(x,z)$ in the expression (7) are obtained. At this point, phase unwrapping is performed (S26). Specifically, since phase variation from 0 to $2\pi$ is repeated, phase unwrapping is performed so that the phase varies in the positive direction toward the optical axis direction.

The control computation unit 4 performs noise reduction using a spatial filter such as a standard deviation filter on the thus obtained tomographic phase distribution $\Phi(x,z)$ (S28), and performs spatial interpolation over the noise-reduced part of the tomographic phase distribution Φ(x,z) (S30). For example, the control computation unit 4 applies the least-squares method for polynomial approximation to the phase difference distribution of a spatial region (region of interest) to obtain an interpolation function in the region of interest.

Subsequently, the control computation unit 4 computes a rate of change of the tomographic phase distribution Φ(x,z), that is, tomographic distribution (cross-sectional distribution) of spatial gradient (∂Φ/∂x,∂Φ/∂z) of the tomographic phase distribution Φ(x,z), by the least-squares method (S32) or the like (S32). The control computation unit 4 uses the thus obtained tomographic distribution of spatial gradient (∂Φ/∂x,∂Φ/∂z) as spatial frequency, and refers to the computation maps of the corresponding material as shown in FIGS. 7A and 7B to calculate stress distribution. The control computation unit 4 then tomographically visualizes the stress distribution (S34).

Figure 10A:
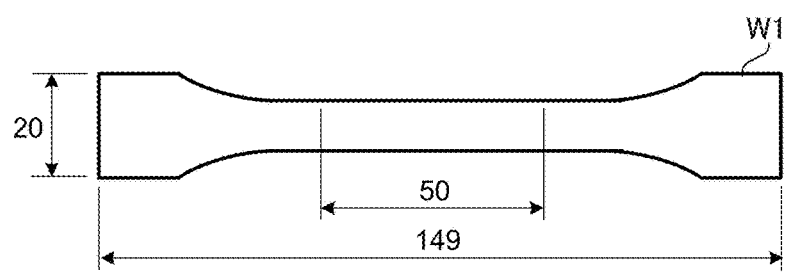
FIGS. 10A and 10B are diagrams illustrating an object W used in experiment and the direction of stress loaded on the object W.
Figure 10B:
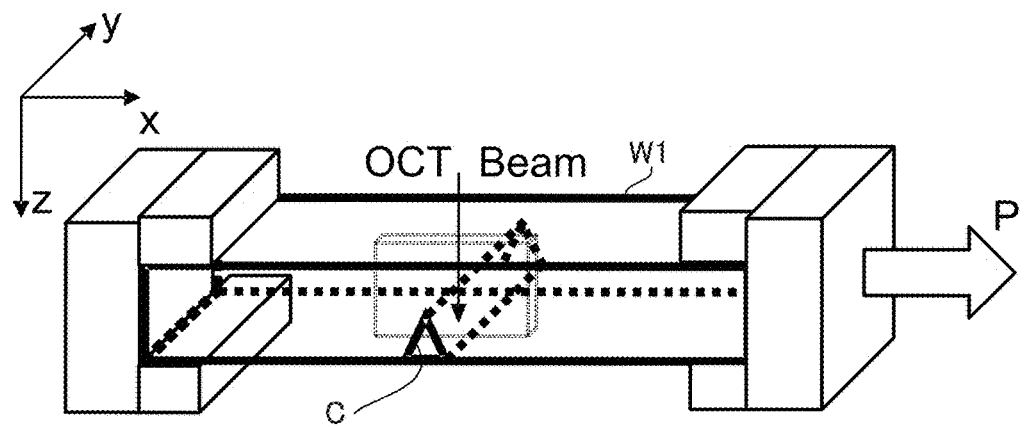
Figure 11A:
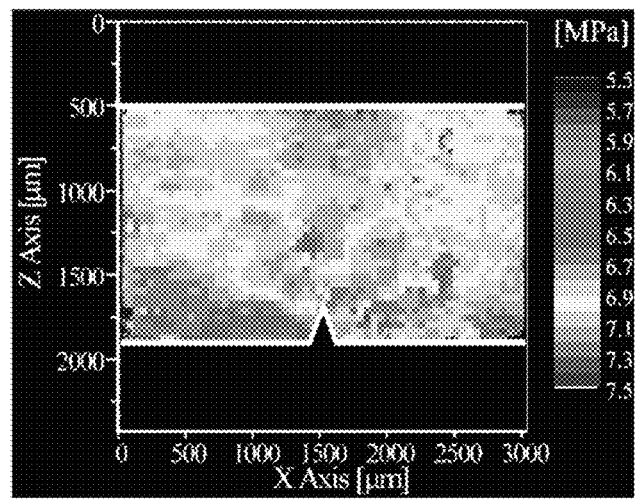
FIGS. 11A to 11C show examples of screens showing stress visualized states.
Figure 11B:
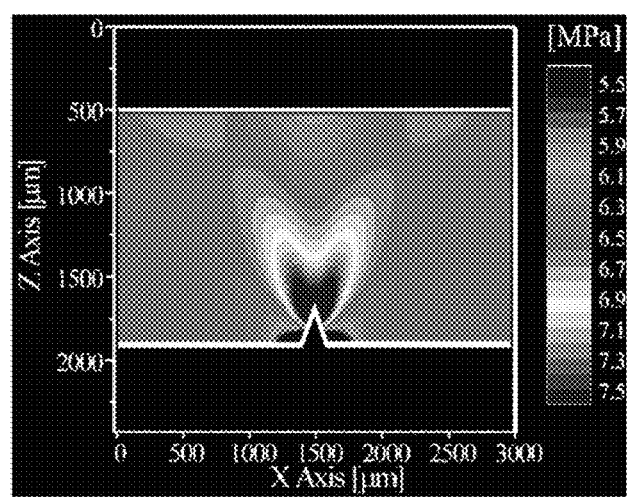
Figure 11C:
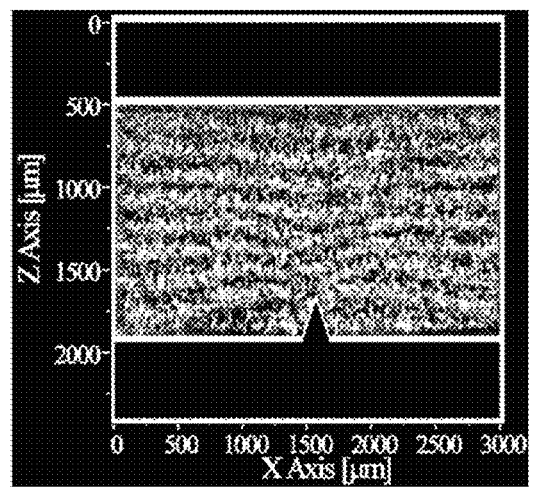

Results of experiment based on a tomographic stress visualization process of the present embodiment will now be presented. FIGS. 10A and 10B illustrate an object W used in the experiment and the direction of stress loaded on the object W. FIG. 10A illustrates a specimen, which is the object W, and FIG. 10B illustrates a loading method. FIGS. 11A to 11C show screens visualizing stress. FIG. 11A illustrates a screen visualizing stress according to the present embodiment. FIG. 11B shows a result of stress analysis by the FEM under the same condition as the present embodiment, as a comparative example. FIG. 11C shows a tomographic image obtained by the PS-OCT before obtaining the image of FIG. 11A. In each of FIGS. 11A to 11C, the horizontal axis represents the position in the x direction, and the vertical axis represents the position in the z direction.

In this experiment, a dumbbell-shaped piece as illustrated in FIG. 10A was used as the specimen W1. The specimen W1 is made of low-density polyethylene having a total length of 149 mm, a maximum width of 20 mm, and a thickness of 1.5 mm. As illustrated in FIG. 10B, the direction in which polarized light was incident by the PS-OCT was defined as a z axis, and an x axis and a y axis were set to be orthogonal to the z axis. The specimen W1 was placed so that an end surface in the thickness direction (depth direction) extends along an x-y plane. In addition, a scanning direction perpendicular to the optical axis of the polarized light was set to the x-axis direction, which was the same direction as the longitudinal direction of the specimen W1. A notch C having a depth of 200 μm was formed in a lower surface in a middle part in the longitudinal direction of the specimen W1 so as to cause stress concentration. The notch C extended linearly in the y axis direction. A tensile load P was applied to the specimen W1 in the longitudinal direction, the specimen W1 was subjected to stress relaxation for 30 minutes, the above-described measurement with the PS-OCT was then performed, and stress was tomographically visualized.

As a result, as shown in FIG. 11A, a tomographic image of stress distribution was visualized. Stress values are shown in a right column in FIG. 11A, and it is recognized that the stress values correspond to those in the result of the FEM analysis shown in FIG. 11B with high precision. While the stress values are visually displayed in FIG. 11A, a tomographic image of $S_3/S_0(x,z)$ can be displayed as shown in FIG. 11C, which allows the spatial frequency of interference fringes at cross-sectional positions to be obtained, and thus allows stress intensity distribution to be recognized.

As described above, according to the present embodiment, application of the phase shifting technique to the PS-OCT enables calculation and visualization of stress at any cross-sectional position of an object W. Thus, stress measurement at any position inside an object W can be performed at the spatial resolution of the OCT. A very high resolution is therefore achieved in visualization of stress distribution.

[Second Embodiment]

A second embodiment will now be described.

In the present embodiment, tomographic distribution of strain rate is computed in addition to the above-described tomographic distribution of stress, and these are used for calculation and visualization of tomographic distribution of mechanical property value at any position inside an object W. The "mechanical property value" used herein is a coefficient obtained from stress and a strain rate (or strain) and includes a modulus of elasticity and a coefficient of viscosity.

First, regarding computation of the tomographic distribution of strain rate, a method for detecting microscale mechanical characteristics using the OCT will be explained. This detection method is a technique of applying a digital cross-correlation method to two OCT images acquired before and after deformation of an object W to calculate distribution of deformation vector, and tomographically detecting distribution of strain rate tensor inside the object in microscale.

For calculation of the distribution of deformation vector, a recursive cross-correlation method of repeating cross-correlation is applied. This is a technique of applying a cross-correlation method by referring to deformation vectors calculated at low resolution, and limiting a search region while hierarchically reducing an interrogation region (subset, inspection region). This enables high-resolution deformation vectors to be obtained. Furthermore, an adjacent cross-correlation multiplication of multiplying correlation value distributions of adjacent interrogation regions is used as a method for reducing speckle noise. Correlation value distribution with a higher SNR obtained by the multiplication is then searched for a maximum correlation value.

In microscale deformation analysis, sub-pixel accuracy of deformation vectors is important. Thus, sub-pixel analysis methods including an upstream gradient method using an intensity gradient and an image deformation method based on expansion/contraction and shear are used to achieve high accuracy detection of deformation vectors. Note that the "upstream gradient method" used herein is one type of gradient methods (optical flow methods).

The thus obtained deformation vectors are differentiated with respect to time for computation of distribution of deformation rate vector, and the distribution of deformation rate vector is then differentiated with respect to space for computation of distribution of strain rate tensor.

Figure 12A:
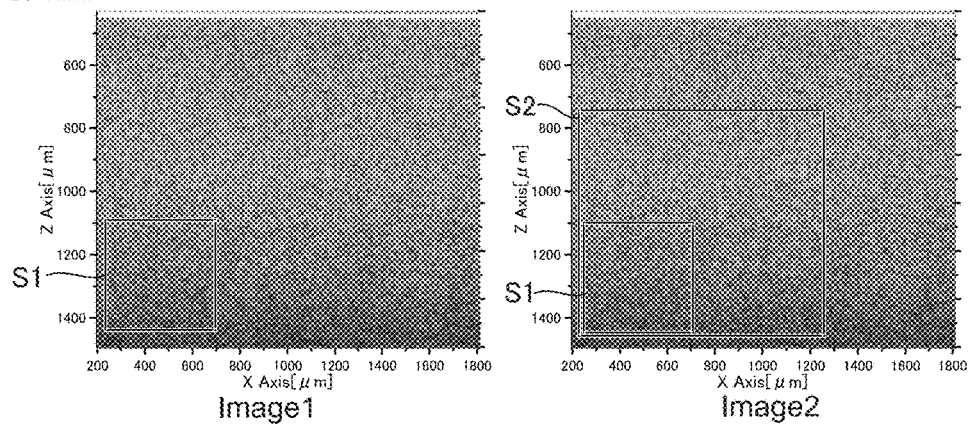
FIGS. 12A to 12C show an outline of procedures of a recursive cross-correlation method.
Figure 12B:
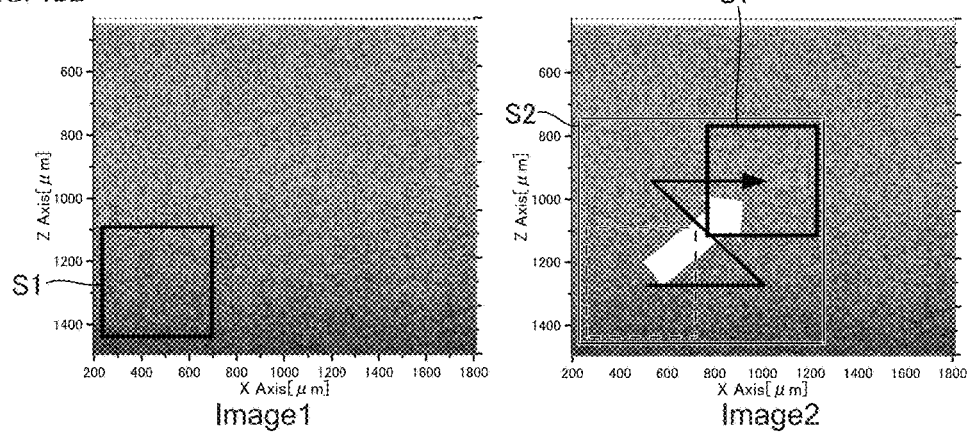
Figure 12C:
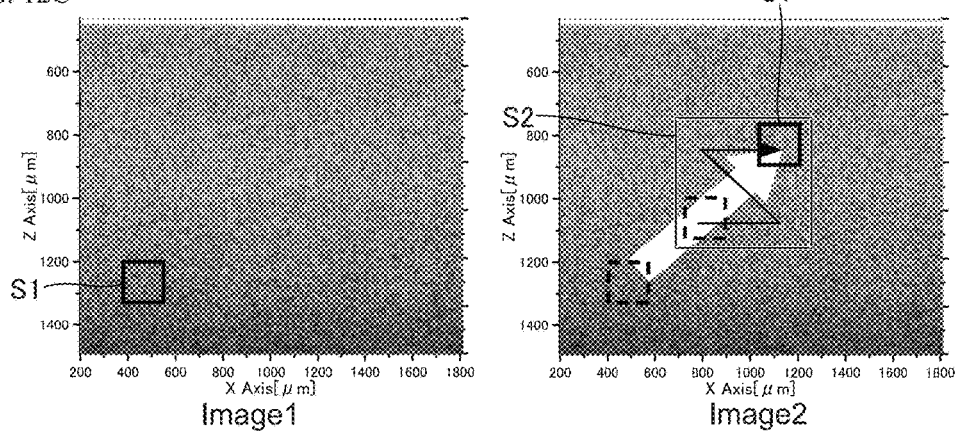
Figure 13A:
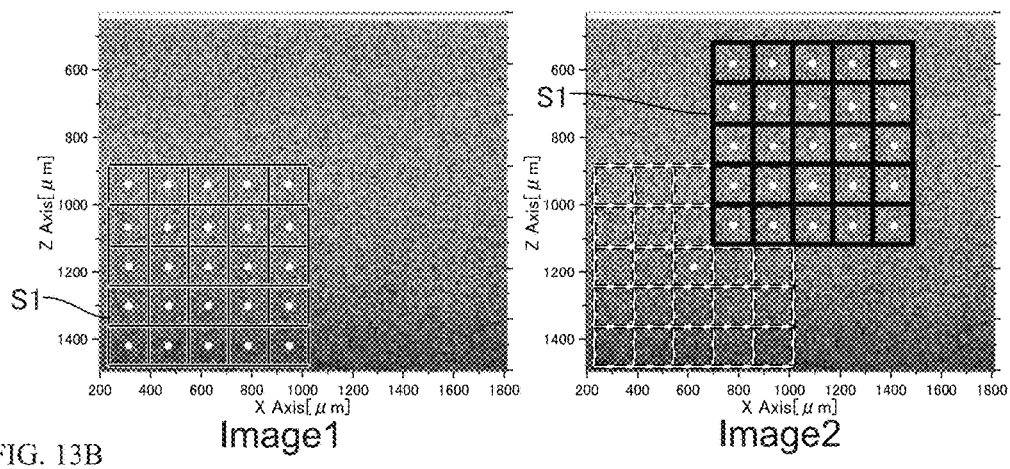
FIGS. 13A to 13C show an outline of procedures of sub-pixel analysis.
Figure 13B:
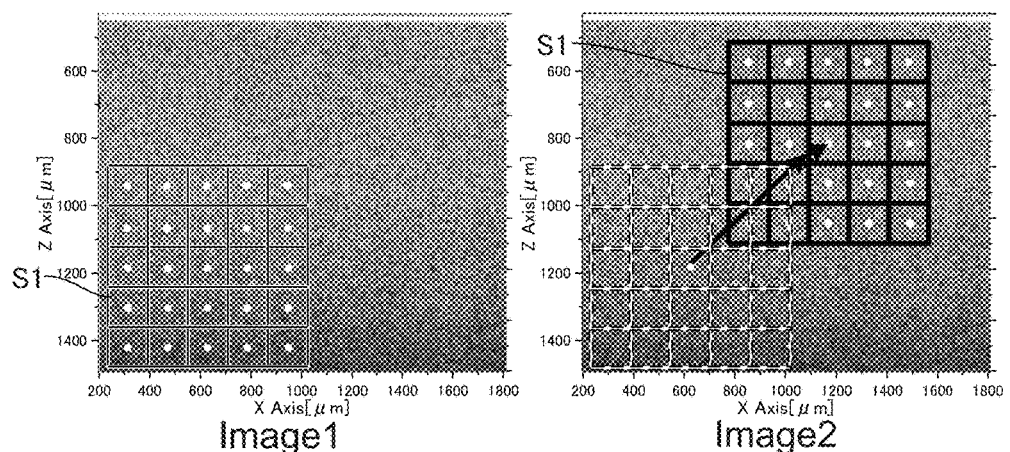
Figure 13C:
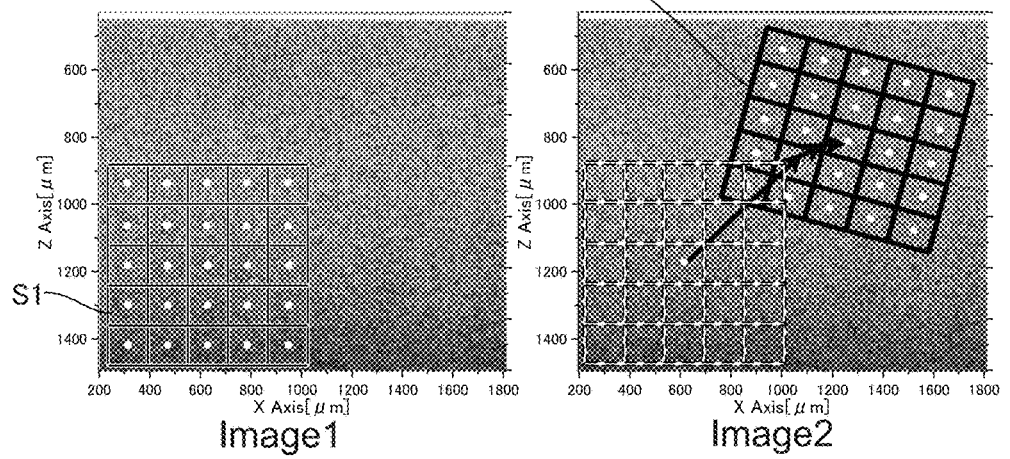

Hereinafter, the respective methods will be described in detail. FIGS. 12A to 12C show an outline of procedures of the recursive cross-correlation method. FIG. 13A to 13C show an outline of procedures of the sub-pixel analysis.

<Recursive Cross-correlation Method>

FIGS. 12A to 12C show processes according to the recursive cross-correlation method. Each of FIGS. 12A to 12C shows tomographic images taken continuously by the OCT. A left image shows a tomographic image (Image 1) taken first, and a right image shows a tomographic image (Image 2) taken next.

A cross-correlation method is a method of evaluating similarity of local speckle patterns by a correlation value $R_{i,j}$ based on the following expression (8). Thus, as shown in FIG. 12A, in the OCT images taken continuously, an interrogation region S1 for similarity inspection is set in the first tomographic image (Image 1), and a search region S2, which is a range for searching similarity, is set in the next tomographic image (Image 2).

$$R_{i,j}(\Delta X, \Delta Z) = \sum_{i=1}^{N_x} \sum_{j=1}^{N_z} \{f(X_i, Z_j) - \bar{f}\} \quad (8)$$

$$\{g(X_i + \Delta X, Z_j + \Delta Z) - \bar{g}\} \times \left(\sum_{i=1}^{N_x} \sum_{j=1}^{N_z} \{f(X_i, Z_j) - \bar{f}\}^2\right)^{-\frac{1}{2}} \times$$

$$\left(\sum_{i=1}^{N_x} \sum_{j=1}^{N_z} \{g(X_i + \Delta X, Z_j + \Delta Z) - \bar{g}\}^2\right)^{-\frac{1}{2}}$$

Note that a spatial coordinate system is set, in which a Z axis is the optical axis direction, and an X axis is perpendicular to the Z axis. $f(X_i, Z_j)$ and $g(X_i, Z_j)$ represent speckle patterns in the interrogation region S1 ($N_x \times N_z$ pixels) at a center position ($X_i, Z_j$) of the OCT images before and after deformation.

Correlation value distribution $R_{i,j}(\Delta X, \Delta Z)$ in the search region S2 ($M_x \times M_z$ pixels) is calculated, and pattern matching is carried out as shown in FIG. 12B. In practice, a displacement $U_{i,j}$ that produces the maximum correlation value is determined to be a deformation vector between before and after deformation as expressed by the following expression (9).

$$\vec{U}_{i,j} = \begin{pmatrix} \Delta X_{max} \\ \Delta Z_{max} \end{pmatrix} = \text{argmax} R_{i,j}(\Delta X, \Delta Z) \quad (9)$$

Note that $\bar{f}$ and $\bar{g}$ represent average values of $f(X_i, Z_j)$ and $g(X_i, Z_j)$ within the interrogation region S1.

This technique employs the recursive cross-correlation method of repeating a cross-correlation process while reducing the interrogation region S1 to increase spatial resolution. Note that, in this example, the resolution is increased such that the spatial resolution is doubled. As shown in FIG. 12C, the interrogation region S1 is divided to be reduced to ¼, the deformation vector calculated in the previous hierarchy is referred to, and the search region S2 is reduced. The search region S2 is also divided to be reduced to ¼. Use of the recursive cross-correlation method prevents or reduces erroneous vectors that are frequently generated at high resolution. Such a recursive cross-correlation process increases the resolution of deformation vectors.

In addition, a threshold using a mean deviation σ of a total of nine deformation vectors including the coordinate being calculated and eight coordinates around the calculated coordinate is set so as to remove erroneous vectors and prevent error propagation due to the recursive processes by the following expression (10).

$$|\vec{U}_{i,j} - \vec{U}_m| < K\sigma \quad (10)$$

In the expression (10), $U_m$ represents a median of vector quantity, and a coefficient K that is the threshold is freely set.

(Adjacent Cross-correlation Multiplication)

In this example, the adjacent cross-correlation multiplication is introduced as a method for determining an accurate maximum correlation value from highly-random correlation value distribution affected by speckle noise. The adjacent cross-correlation multiplication multiplies the correlation value distribution $R_{i,j}(\Delta x, \Delta z)$ in the interrogation region S1 by $R_{i+\Delta i, j}(\Delta x, \Delta z)$ and $R_{i, j+\Delta j}(\Delta x, \Delta z)$ for adjacent interrogation regions overlapping with the interrogation region S1 to search for a maximum correlation value by using a new correlation value distribution $R'_{i,j}(\Delta x, \Delta z)$, as expressed by the following expression (11).

$$R'_{i,j}(\Delta x, \Delta z) = R_{i,j}(\Delta x, \Delta z) \times R_{i+\Delta i, j}(\Delta x, \Delta z) \times R_{i, j-\Delta j}(\Delta x, \Delta z) \quad (11)$$

As a result, the multiplication of the correlation values enables reduction in the randomness. Since the amount of information of interference intensity distribution is also reduced with the aforementioned reduction in size of the interrogation region S1, occurrence of multiple correlation peaks caused by speckle noise is considered to result in degradation in measurement accuracy. In contrast, since the displacements of adjacent boundaries are correlated, a high correlation value remains near the coordinates of the maximum correlation value. The introduction of the adjacent cross-correlation multiplication makes the maximum correlation peak clearer, improves the measurement accuracy, and accurately extracts displaced coordinates. In addition, introduction of the adjacent cross-correlation multiplication at respective stages of the OCT prevents or reduces error propagation, and improves robustness to speckle noise. As a result, accurate deformation vectors and strain distribution can be calculated even at high spatial resolution.

<Upstream Gradient Method>

FIGS. 13A to 13C show processes according to sub-pixel analysis. Each of FIGS. 13A to 13C shows tomographic images taken continuously by the OCT. A left image shows a tomographic image (Image 1) taken first, and a right image shows a tomographic image (Image 2) taken next.

In this example, an upstream gradient method and an image deformation method are used for the sub-pixel analysis. Although a final displacement is calculated by the image deformation method to be described below, the upstream gradient method is applied prior to the image deformation method for the reason of convergence of calculations. The image deformation method and the upstream gradient method for detecting a sub-pixel displacement with high accuracy are applied under a condition where the interrogation region size is small and the spatial resolution is high. In a case where detection of a sub-pixel displacement by the image deformation method is difficult, the sub-pixel displacement is calculated by the upstream gradient method.

In the sub-pixel analysis, an intensity difference between before and after deformation at a point of interest is expressed by the intensity gradients of respective components and the displacement. Thus, the sub-pixel displacement can be determined by using the least-squares method from intensity gradient data in the interrogation region S1. In this example, for obtaining an intensity gradient, an upwind difference method that provides an upwind intensity gradient before sub-pixel deformation is used.

Specifically, while there are various techniques for sub-pixel analysis, the gradient method that detects the sub-pixel displacement with high accuracy even under the condition where the interrogation region size is small and the spatial resolution is high is used in this example.

The upstream gradient method is a technique for calculating displacement of a point of interest within the interrogation region S1 not just with pixel accuracy as shown in FIG. 13A but with sub-pixel accuracy as shown in FIG. 13B. Note that each square in FIGS. 13A to 13C represents one pixel. Although the pixels are actually significantly smaller than the shown tomographic images, the pixels are illustrated in a large size for convenience of explanation. The upstream gradient method is a technique of formulating a change in intensity distribution between before and after small deformation by using the intensity gradient and the displacement, and is expressed by the following expression (12) that calculates the Taylor expansion of small deformation $f(x+\Delta x, z+\Delta z)$ where f represents the intensity.

$$f_x(x,z)\Delta x + f_z(x,z)\Delta z = f(x+\Delta x, z+\Delta z) - f(x,z) \quad (12)$$

The expression (12) shows that the intensity difference at the point of interest between before and after deformation is expressed by the intensity gradient before the deformation and the displacement. Note that, since the displacement $(\Delta x, \Delta z)$ cannot be determined only by the expression (12), the displacement within the interrogation region S1 is assumed to be constant and the least-squares method is applied for the calculation.

In calculation of the displacement by using the expression (12), the intensity difference at each point of interest between before and after displacement on the right side of the expression (12) is obtained only uniquely. Thus, the accuracy of intensity gradient calculation is directly linked to the accuracy of the displacement. For differencing of the intensity gradient, first-order upwind difference is used. This is because a large amount of data will be required and the influence of contained noise, if any, will be great if a high-order difference is applied to differencing. This is also because a large amount of data outside of the interrogation region S1 will be used in a high-order difference based on a point in the interrogation region S1, which poses a problem that the obtained displacement will not be an amount of the interrogation region S1 itself.

In obtaining the intensity gradient, since it can be assumed that the displacement of an upwind intensity gradient before deformation causes an intensity difference at a point of interest, an upwind difference is applied before deformation. The term upwind used herein does not mean the actual displacement direction but means the direction of a sub-pixel displacement with respect to a pixel displacement, and the upwind direction is determined by applying parabolic approximation to the maximum correlation peak. Conversely, since it can be assumed that the reverse displacement of a downwind intensity gradient after deformation causes an intensity difference at a point of interest, a downwind difference is applied after deformation.

Two solutions are found by using the upwind difference before deformation and the downwind difference after deformation, and an average of the solutions is obtained. Furthermore, the intensity gradients before and after deformation are not actually on the same axis as the points of interest if the displacements are not along the axial direction, and gradients at shifted positions need to be obtained. Specifically, for obtaining a gradient in the X direction, displacement in the Z direction need to be taken into consideration. Thus, the intensity gradient is estimated by intensity interpolation, so as to improve the accuracy. Basically, a position before (or after) deformation is estimated, and the gradient at the position is obtained by interpolation.

The position of a point of interest before (or after) deformation is obtained from the sub-pixel displacement when the parabolic approximation is applied.

Eight coordinates surrounding the point of interest position are used, and the intensity gradient is calculated from the ratios of the intensities at the eight coordinates to the intensity at the point of interest. Specifically, the following expression (13) is used. The least-squares method is applied using the thus calculated intensity gradient and an intensity change to determine the displacement.

$$f_x(x,z) = \Delta z \{f(x,z-1) - f(x-1,z-1)\} + (1-\Delta z)\{f(x,z) - f(x-1,z)\} \quad (13)$$

<Image Deformation Method>

In the calculation of deformation vectors until the upstream gradient method described above, the shape of the interrogation region S1 has not been changed and remains square. In reality, however, since the interrogation region S1 is likely to be deformed with the deformation of the object, an algorithm based on small deformation of the interrogation region S1 needs to be introduced for calculation of deformation vectors with high accuracy. Thus, in this example, the image deformation method is introduced for calculation of deformation vectors with sub-pixel accuracy. Specifically, cross-correlation between the interrogation region S1 before deformation of the material and the interrogation region S1 after the deformation where expansion/contraction and shear deformation is considered is performed, and a sub-pixel deformation quantity is determined by repeated calculation based on the correlation value. Note that the expansion/contraction and shear deformation of the interrogation region S1 is linearly approximated.

The image deformation method is typically used for surface strain measurement of a material, and applied to an image of a material surface coated with a random pattern taken by a high spatial resolution camera. In contrast, since an OCT image contains much speckle noise and since a composite material is locally deformed, the convergence of the solution is significantly lowered if the interrogation region S1 is deformed. The reduction of the interrogation region S1 in the present technique is essential for detection of a local, mechanical characteristic. Thus, in the image deformation method, the deformation quantity obtained by the upstream gradient method is used as an initial value for convergence calculation, and bicubic interpolation of the intensity distribution is further used, to achieve low robustness even when the interrogation region S1 is reduced. Alternatively, in a modification, an interpolation function other than the bicubic interpolation may be used.

More specifically, the computation is performed according to the following procedures. First, the bicubic interpolation is applied to the intensity distribution of the OCT image before the material deformation, to make the intensity distribution continuous. The bicubic interpolation is a technique of using a convolution function obtained by piecewise approximation of cubic polynomial function of a sinc function, to reproduce spatial continuity of intensity information. Since a point spread function dependent on an optical system is convolved in image measurement of intensity distribution, which is originally continuous, the originally continuous intensity distribution is reproduced by deconvolution using the sinc function. For interpolation of a single-axis, discrete signal $f(x)$, a convolution function $h(x)$ is expressed by the following expression (14).

$$h(x) = \begin{cases} (a+2)|x|^3 - (a+3)|x|^2 + 1 & (|x| \leq 1) \\ a|x|^3 - 5a|x|^2 + 8a|x| - 4a & (1 \leq |x| \leq 2) \\ 0 & (|x| \geq 2) \end{cases} \quad (14)$$

Note that the shape of the interpolation function $h(x)$ needs to be changed depending on the difference in OCT measurement condition. An algorithm in which a derivative a of the intensity interpolation function $h(x)$ where $x=1$ is made to be variable and in which the shape of the intensity interpolation function $h(x)$ is changeable by changing the value a is thus provided. In this example, the value a is determined on the basis of a result of verification by numerical experiment using a pseudo-OCT image. The image interpolation as described above allows an OCT intensity value to be obtained at each point in the interrogation region S1 where expansion/contraction and shear modification is considered.

The interrogation region S1 calculated in view of expansion/contraction and shear deformation is deformed with displacement as shown in FIG. 13C. When it is assumed that coordinates (x,z) at an integer pixel position in an interrogation region S1 of an OCT image before material deformation are displaced to coordinates (x*,z*), the values of x* and z* are expressed by the following expression (15).

$$\begin{cases} x^* = x + \Delta x + u + \frac{\partial u}{\partial x}\Delta x + \frac{\partial u}{\partial z}\Delta z \\ z^* = z + \Delta z + v + \frac{\partial v}{\partial x}\Delta x + \frac{\partial v}{\partial z}\Delta z \end{cases} \quad (15)$$

In the expression (15), $\Delta x$ and $\Delta z$ represent the distances from the center of the interrogation region S1 to coordinates x and z, respectively, u and v represent deformation quantities in the x and z directions, respectively, $\partial u/\partial x$ and $\partial v/\partial z$ represent vertical strains in the x and y directions of the interrogation region S1, respectively, and $\partial u/\partial z$ and $\partial v/\partial x$ represent shear strains in the x and y directions of the interrogation region S1, respectively. The Newton-Raphson method is used for numerical solution, and repeated calculation is carried out so that the correlation value derivative with six variables (u, v, $\partial u/\partial x$, $\partial u/\partial z$, $\partial v/\partial x$, and $\partial v/\partial z$) becomes 0, that is, so that the maximum correlation value is obtained. In order to increase the convergence of the repeated calculation, sub-pixel displacements obtained by the upstream gradient method are used for displacement initial values in the x and z directions. When a Hessian matrix for a correlation value R is represented by H, and a Jacobi vector for the correlation value is represented by $\nabla R$, an update amount $\Delta P_i$ obtained at each repetition is expressed by the following expression (16).

$$\Delta P_i = -H^{-1}\nabla R \quad (16)$$

The determination of convergence is based on the fact that the asymptotic solution obtained at each repetition of calculation becomes sufficiently small near the convergent solution. In a region where the speckle pattern changes drastically, however, a correct convergent solution may not be obtained because the change cannot be tracked by linear deformation. In this case, the sub-pixel displacement obtained by the upstream gradient method is used in this example.

The deformation vectors with sub-pixel accuracy obtained as described above are differentiated with respect to time, which enables calculation of distribution of deformation rate vector. The distribution of deformation rate vector is then differentiated with respect to space, which enables calculation of a strain rate tensor.

<Temporal/Spatial Moving Least-squares Method>

For calculation of a strain rate tensor, the moving least-squares method (hereinafter referred to as the "MLSM") is used. The MLSM is a technique allowing smoothing of displacement distribution and stable calculation of a derivative. A squared error equation used in the MLSM is expressed by the following expression (17).

$$S(x, z, t) = \sum_{n=1}^{N} \sum_{m=1}^{M} \sum_{l=1}^{L} [y(x_n, z_m, t_l) - f(x_n, z_m, t_l)]^2 \quad (17)$$

In the expression (17), parameters a to k with which S(x,z,t) is minimized are obtained. Specifically, the expression (18) below is used as a quadratic polynomial with three variables in the horizontal direction x, the depth direction z and the time direction t for the approximation function. An optimum derivative is then calculated by the following expression (19) on the basis of the least squares approximation, and smoothing is performed.

$$f(x_n, z_m, t_l) = \quad (18)$$
$$ax_n^2 + bz_m^2 + ct_l^2 + dx_n z_m + ex_n t_l + gz_m t_l + hx_n + iz_m + jt_l + k$$

$$\begin{pmatrix} \frac{\partial S(x, y, z)}{\partial a} \\ \vdots \\ \frac{\partial S(x, y, z)}{\partial k} \end{pmatrix} + \begin{pmatrix} \frac{\partial^2 S(x, y, z)}{\partial a^2} & \cdots & \frac{\partial^2 S(x, y, z)}{\partial a \partial k} \\ \vdots & \ddots & \vdots \\ \frac{\partial^2 S(x, y, z)}{\partial k \partial a} & \cdots & \frac{\partial^2 S(x, y, z)}{\partial k^2} \end{pmatrix} \begin{pmatrix} a \\ \vdots \\ k \end{pmatrix} = \begin{pmatrix} 0 \\ \vdots \\ 0 \end{pmatrix} \quad (19)$$

The strain rate tensor expressed by the following expression (20) can be calculated by using this derivative. $f_x$ and $f_z$ represent the amounts by which strain is increased along the respective axes. The strain rate is calculated from the amounts of strain changes with respect to time.

$$\frac{\partial \epsilon}{\partial t} = \frac{\partial}{\partial t} \begin{pmatrix} \frac{\partial f_x}{\partial x} & \frac{\partial f_z}{\partial x} \\ \frac{\partial f_x}{\partial z} & \frac{\partial f_z}{\partial z} \end{pmatrix} \quad (20)$$

Figure 14A:
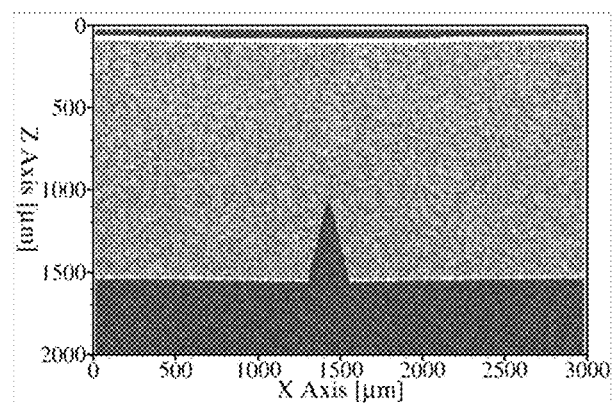
FIGS. 14A to 14C show procedures of a process of tomographic visualization of a mechanical property value.
Figure 14B:
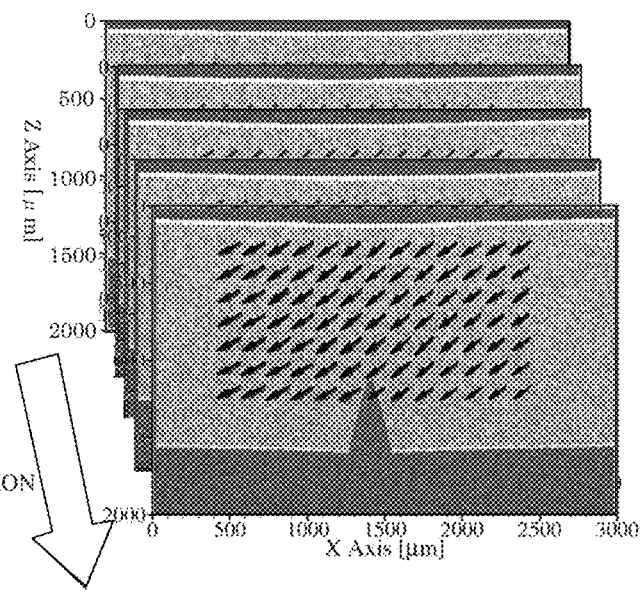
Figure 14C:
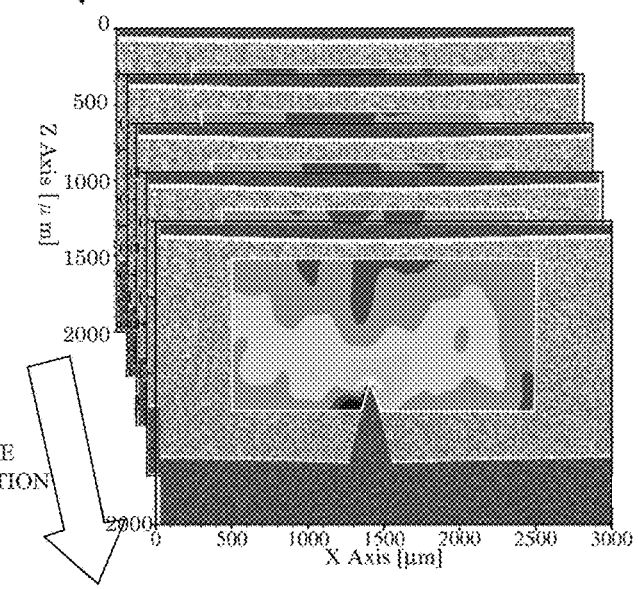

A process of tomographic visualization of a mechanical property value by using the distribution of strain rate obtained as described above and the distribution of stress obtained in the first embodiment is performed. An example according to the present embodiment will now be described. FIGS. 14A to 14C show procedures of the process of tomographic visualization of the mechanical property value. Tomographic images in FIGS. 14A to 14C show results of experiment using the specimen W1 shown in FIGS. 10A to 11C as the object W.

The control computation unit 4 continuously acquires tomographic images of the object W (FIGS. 14A and 14B), sequentially stores the distributions of deformation rate vector computed as described above (FIG. 14B), and sequentially stores the distributions of strain rate tensor obtained by spatial differentiation of each of the distributions of deformation rate vector (FIG. 14C). Note that each distribution of strain rate tensor can be displayed in a form of a tomographic image of a predetermined range in an identifiable manner as shown in FIG. 14C.

Figure 15A:
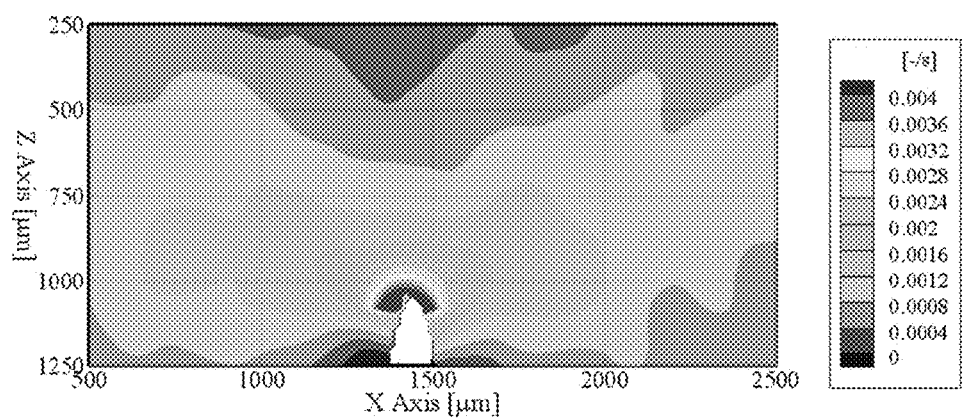
FIGS. 15A and 15B show screens visualizing strain rates.
Figure 15B:
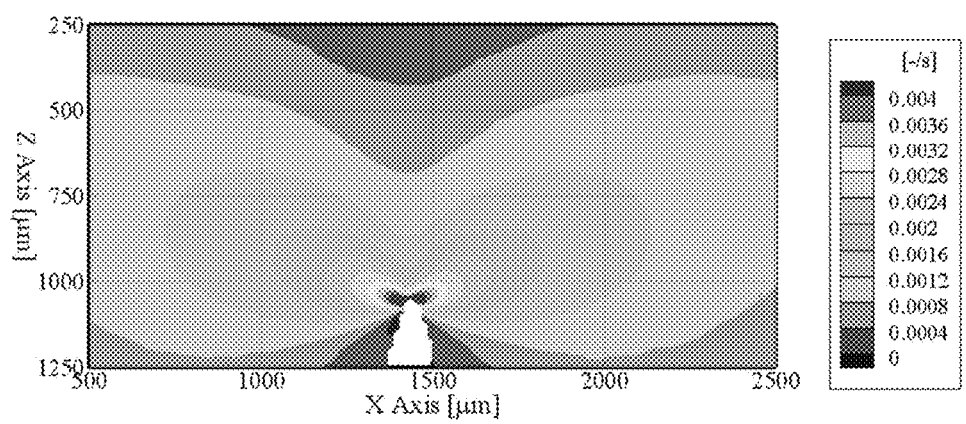

FIGS. 15A and 15B show screens visualizing the strain rate. FIG. 15A shows a screen visualizing the strain rate according to the present embodiment. FIG. 15B shows a result of strain rate analysis by the FEM under the same condition as the present embodiment, as a comparative example. In each of FIGS. 15A and 15B, the horizontal axis represents the position in the x direction, and the vertical axis represents the position in the z direction.

Regarding computation and visualization of the strain rate distribution, it is recognized in FIGS. 15A and 15B that the result of computation by the OCT according to the present embodiment corresponds to the result of the FEM analysis with high precision. Since a highly precise result is obtained for the stress distribution as mentioned in the first embodiment, the tomographic distribution of mechanical property value is obtained with high accuracy on the basis of the stress distribution and the strain rate distribution.

Next, specific procedures of the process performed by the control computation unit 4 will be explained.

Figure 16:
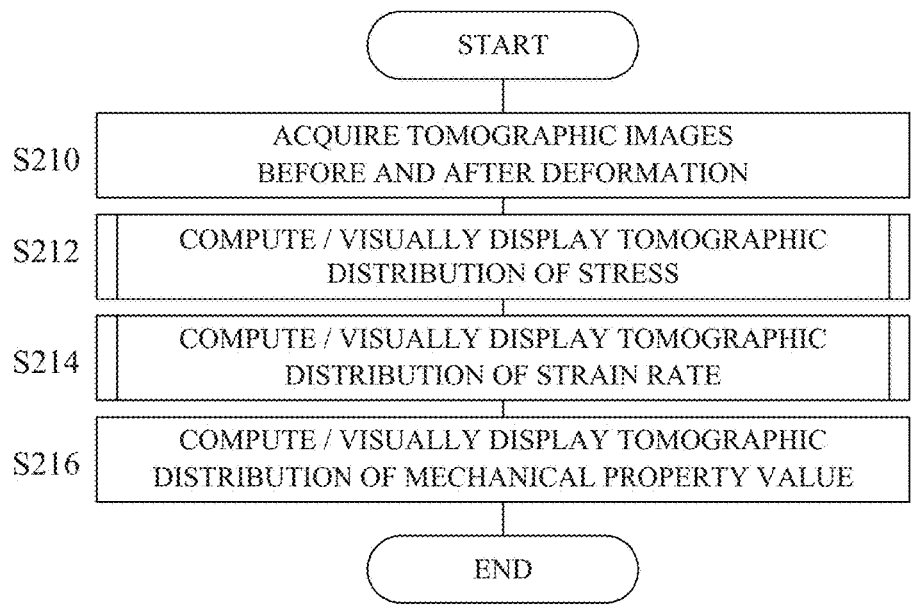
FIG. 16 is a flowchart illustrating procedures of a physical quantity visualization process performed by the control computation unit.

FIG. 16 is a flowchart illustrating the procedures of a mechanical property value visualization process performed by the control computation unit 4. The control computation unit 4 continuously acquires tomographic images of an object W by the OCT (S210). The control computation unit 4 then computes tomographic distribution of stress by using the tomographic images, and displays the tomographic distribution of stress on a screen (S212). The control computation unit 4 also computes tomographic distribution of strain rate by using the tomographic images, and displays the tomographic distribution of strain rate on a screen (S214). The control computation unit 4 then computes tomographic distribution of mechanical property value from the results of computation of the tomographic distribution of stress and the tomographic distribution of strain rate, and displays the tomographic distribution of mechanical property value on a screen (S216). Note that the process of the first embodiment can be applied to the computation process and the like of the tomographic distribution of stress in S212. The explanation thereof is therefore omitted here.

Figure 17:
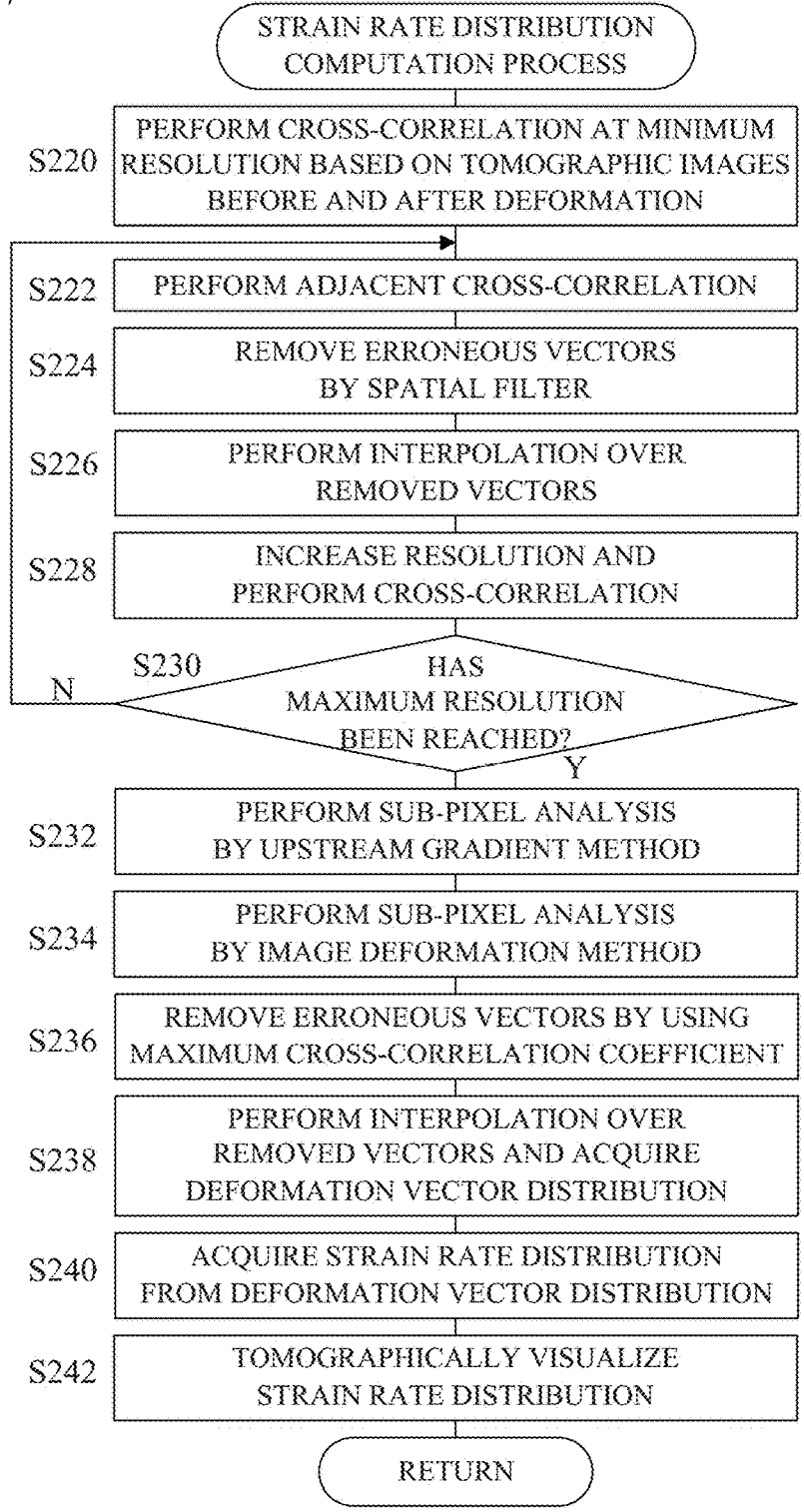
FIG. 17 is a flowchart illustrating a process of computation and visualization of strain rate distribution in S214 of FIG. 16 in detail.

FIG. 17 is a flowchart illustrating the processes for computation/visualization of the strain rate distribution in S214 of FIG. 16 in detail. The control computation unit 4 acquires two OCT images I(x,z,t) and I(x,z,t+Δt) continuously taken at times different from each other, and performs a process by the recursive cross-correlation method (S220). Each of the OCT images is obtained as a sum of squares of the horizontal polarization component $I_H(x,z)$ and the vertical polarization component $I_V(x,z)$ acquired in S10 of FIG. 9. Thus, the Stokes parameter $S_0$ of the expression (4) corresponds to the OCT image.

In this process, the control computation unit 4 first performs cross-correlation at minimum resolution (an interrogation region of the maximum size), and obtains correlation coefficient distribution. Subsequently, the control computation unit 4 computes a product of adjacent correlation coefficient distributions by adjacent cross-correlation multiplication (S222). At this point, the control computation unit 4 removes erroneous vectors by a spatial filter such as a standard deviation filter (S224), and performs interpolation over the removed vectors by the least-squares method or the like (S226). Subsequently, the control computation unit 4 reduces the interrogation region in size to increase the resolution, and continue the cross-correlation (S228). Thus, cross-correlation is performed on the basis of a reference vector at low resolution. If the resolution at this point has not reached a predetermined maximum resolution (N in S230), the control computation unit 4 returns to S222.

The control computation unit 4 then repeats the processing in S222 to S228, and when the cross-correlation is completed at the maximum resolution (Y in S230), performs sub-pixel analysis. Specifically, the control computation unit 4 computes a sub-pixel displacement by the upstream gradient method on the basis of the distribution of deformation vector at the maximum resolution (the interrogation region of the minimum size) (S232). The control computation unit 4 then computes a sub-pixel deformation quantity by the image deformation method on the basis of the obtained sub-pixel displacement (S234). Subsequently, the control computation unit 4 removes erroneous vectors by filtering using a maximum cross-correlation value (S236), and performs interpolation over the removed vectors by the least-squares method or the like (S238). The control computation unit 4 then differentiates the thus obtained deformation vectors with respect to time to calculate tomographic distribution of deformation rate vector of the tomographic image. The control computation unit 4 then differentiates the deformation rate vectors with respect to space to obtain strain rate distribution (S240), and tomographically visualizes the strain rate distribution on the display device (S242).

Then, in S216 of FIG. 16, the control computation unit 4 computes tomographic distribution of mechanical property value from the computation results of the tomographic distribution of stress and the tomographic distribution of strain rate, and displays the tomographic distribution of mechanical property value on a screen. Specifically, the control computation unit 4 can calculate the tomographic distribution of mechanical property value such as the modulus of elasticity by dividing the tomographic distribution data of stress by the tomographic distribution data of strain rate (or tomographic distribution data of strain), and visually display the tomographic distribution of mechanical property value.

In this process, the stress distribution obtained in S212 and the strain rate distribution obtained in S214 are associated with each other as both being based on the same tomographic images acquired in S210. Thus, the tomographic distribution of stress in S212 and the tomographic distribution of strain rate in S214 are obtained substantially concurrently. Then, the tomographic distribution of mechanical property value can be calculated by the above-described division at the corresponding cross-sectional positions in the tomographic distribution of stress and the tomographic distribution of strain rate.

In the present embodiment, computation using continuously acquired tomographic images is performed. Alternatively, in a modification, computation may be performed using successive tomographic images acquired at predetermined time intervals. For example, tomographic distribution of mechanical property value may be calculated by performing average approximation on a tomographic image acquired at time t1 and a tomographic image acquired at time t2. Specifically, stress distributions at time t1 and time t2 may be computed from the tomographic images at time t1 and time t2, respectively, and stress distribution at time t=(t1+t2)/2 may be obtained by average approximation or the like. In the meantime, strain rate (strain) distribution at time t=(t1+t2)/2 may be obtained from the tomographic images at time t1 and time t2. Then, physical property parameters such as a coefficient of viscosity or a modulus of elasticity may be calculated as tomographic distribution of mechanical property value from spatial information of both strain and stress measured concurrently in this manner, and the tomographic distribution of mechanical property value may be visually displayed.

As described above, the present embodiment allows microscale visualization of tomographic distribution of stress and tomographic distribution of strain rate, and further allows visualization of tomographic distribution of mechanical property value from the tomographic distribution of stress and the tomographic distribution of strain rate. Specifically, a system capable of tomographically detecting distributions stress and strain inside a polymer-based material at the same time and further tomographically visualizing a dynamic modulus of elasticity can be built. The present embodiment provides a technology capable of readily measuring and visualizing distribution of stress and distribution of strain applied to an object, and also distribution of mechanical property value of the object by optical techniques without altering the properties of the object.

The description of the present invention given above is based upon illustrative embodiments. The embodiments are intended to be illustrative only and it will be obvious to those skilled in the art that various modifications could be further developed within the technical idea underlying the present invention.

In the above-described embodiments, an example in which two-axis tomographic images $I_H(x,z)$ and $I_V(x,z)$ are acquired in S10 of FIG. 9 and the stress distribution is visualized two-dimensionally on an x-z plane in S34 is presented. In a modification, a single-axis tomographic image $I_H(z)$ may be acquired for a specific x coordinate, and visualized as stress distribution in the z direction.

The technical idea of the second embodiment can be expressed as follows, for example.

A mechanical property value visualization device for visualizing tomographic distribution of mechanical property value of an object, the mechanical property value visualization device including:

an optical unit including an optical system using optical coherence tomography (OCT);

a loading device configured to apply deformation energy (load) to deform the object;

a control computation unit configured to control driving of the optical unit and the loading device, process an optical interference signal output from the optical unit by driving the optical unit and the loading device, and perform a computation; and a display device configured to display a result of the computation by the control computation unit, wherein the control computation unit computes tomographic distribution of stress in the object on a basis of the optical interference signal obtained by driving the optical unit, wherein the control computation unit computes distribution of deformation rate vector (or distribution of deformation vector) at cross-sectional positions of the object resulting from application of the deformation energy on a basis of the optical interference signal obtained by driving the optical unit and the loading device, and computes tomographic distribution of strain rate tensor (or strain tensor) on a basis of the distribution of deformation rate vector (or the distribution of deformation vector), and the control computation unit computes the tomographic distribution of mechanical property value from a result of computation of the tomographic distribution of stress and a result of computation of the tomographic distribution of strain rate tensor (or strain tensor), and visually displays the tomographic distribution of mechanical property value on the display device.

Note that the "loading device" may be a loading mechanism capable of applying a predetermined load on an object, or may be a device for applying a load (exciting force) caused by ultrasonic waves, photoacoustic waves, electromagnetic waves, or the like to an object. The control computation unit may compute tomographic distribution of stress by using the phase shifting technique presented in the first embodiment, or may compute tomographic distribution of stress without using the phase shifting technique. In the latter case, driving of the loading device may be essential in computation of stress distribution. The OCT may be the PS-OCT or may be another OCT. Furthermore, the object is not limited to a polymer-based material but may be other material structures. Alternatively, the object may be a biological structure (body tissue) such as a cartilage or a lump (hard spot). Tomographic visualization of changes in the mechanical characteristics of biological structures provides materials for the diagnosis of many cases such as arteriosclerosis, cancer, cirrhosis, skin, cartilage, bone, and the like.

The present invention is not limited to the above-described embodiments and modifications only, and the components may be further modified to arrive at various other embodiments without departing from the scope of the invention. Various other embodiments may be further achieved by combining, as appropriate, a plurality of structural components disclosed in the above-described embodiment and modifications. Furthermore, one or some of all of the components exemplified in the above-described embodiment and modifications may be left unused or removed.

What is claimed is:

1. A stress visualization device for tomographically visualizing stress in an object to be measured, the stress visualization device comprising:

a light source configured to emit light;

a polarizer configured to linearly polarize the light emitted from the light source;

a beam splitter configured to split the linearly polarized light into a first beam directed to an object arm including the object and a second beam directed to a reference arm including a reference mirror;

an optical modulator provided on the object arm which is controlled to adjust a polarization state of the linearly polarized light;

an optical detection device configured to detect interference light, resulting from superimposition of object light reflected by the object and reference light reflected by the reference mirror, as an optical interference signal, and separate the interference signal into a horizontal polarization component and a vertical polarization component;

a control computation unit connected to the optical modulator to adjust the polarization state by controlling the optical modulator, and configured to compute distribution of stress at cross-sectional positions, each defined by a position in a depth direction and a position in a direction orthogonal to the depth direction of the object, on a basis of a phase difference between the horizontal polarization component and the vertical polarization component of the interference signal detected by the optical detection device; and a display device connected to the control computation unit and configured to display tomographically visualized stress distribution of the object on a basis of a computation result of the control computation unit, wherein the control computation unit controls the optical modulator to change the polarization state to shift a phase of polarized light with which the object is irradiated, computes the phase difference for the interference signal obtained by each phase shift of the polarized light, computes spatial gradients of tomographic distribution of phase difference on a basis of the computed phase differences, and controls the visual display unit to visually display tomographic distribution of spatial gradient in association with tomographic distribution of stress on the display device.

2. The stress visualization device according to claim 1, wherein the control computation unit holds a computation map including preset associations between spatial gradients of phase differences of possible interference signals and stress values for respective kinds of materials of the object, and wherein the control computation unit computes a spatial gradient of tomographic phase difference distribution of the interference signal, then calculates stress by referring to the computation map on a basis of a result of the computation, and tomographically visualizes stress distribution that is a result of the calculation.

3. The stress visualization device according to claim 1, wherein the stress visualization device visually displays internal residual stress of the object without applying external load to the object.

4. The stress visualization device according to claim 1, wherein the object is a polymer-based material.

5. A mechanical property value visualization device for visualizing tomographic distribution of mechanical property value of an object to be measured, the mechanical property value visualization device comprising:

an optical unit including an optical system using optical coherence tomography, the optical unit including an optical modulator;

a loading device configured to apply deformation energy to deform the object;

a control computation unit connected to the optical modulator for controlling a polarization state and configured to control driving of the optical unit and the loading device, process an optical interference signal output from the optical unit by driving the optical unit and the loading device, and perform a computation; and a display device connected to the control computation unit and configured to display a result of the computation by the control computation unit, wherein the control computation unit computes tomographic distribution of stress in the object on a basis of the optical interference signal obtained by driving the optical unit to control the optical modulator, wherein the control computation unit computes distribution of deformation rate vector or distribution of deformation vector at cross-sectional positions of the object resulting from application of the deformation energy on a basis of the optical interference signal obtained by driving the optical unit and the loading device, and computes tomographic distribution of strain rate tensor or strain tensor on a basis of the distribution of deformation rate vector or the distribution of deformation vector, and wherein the control computation unit computes the tomographic distribution of mechanical property value from a result of computation of the tomographic distribution of stress and a result of computation of the tomographic distribution of strain rate tensor or strain tensor, and controls the display device to visually display the tomographic distribution of mechanical property value on the display device.

6. The mechanical property value visualization device according to claim 5, wherein the control computation unit computes distribution of deformation vector at cross-sectional positions of the object, and computes tomographic distribution of strain tensor on a basis of the distribution of deformation vector, and wherein the control computation unit computes tomographic distribution of modulus of elasticity as the mechanical property value, from a result of computation of the tomographic distribution of stress and a result of computation of the tomographic distribution of strain tensor, and visually displays the tomographic distribution of modulus of elasticity on the display device.

7. The mechanical property value visualization device according to claim 5, wherein the control computation unit computes distribution of deformation rate vector at cross-sectional positions of the object, and computes tomographic distribution of strain rate tensor on a basis of the distribution of deformation rate vector, and wherein the control computation unit computes tomographic distribution of coefficient of viscosity as the mechanical property value from a result of computation of the tomographic distribution of stress and a result of computation of the tomographic distribution of strain rate tensor, and visually displays the tomographic distribution of coefficient of viscosity on the display device.

* * * * *